United States Patent
Michaeli

(10) Patent No.: US 8,486,910 B2
(45) Date of Patent: Jul. 16, 2013

(54) SNORNAI-SMALL NUCLEOLAR RNA DEGRADATION BY RNA INTERFERENCE IN TRYPANOSOMATIDS

(75) Inventor: Shulamit Michaeli, Kiryat Ono (IL)

(73) Assignee: Bar-Ilan University, Ramat-Gan (IL)

( * ) Notice: Subject to any disclaimer, the term of this patent is extended or adjusted under 35 U.S.C. 154(b) by 0 days.

(21) Appl. No.: 13/417,357

(22) Filed: Mar. 12, 2012

(65) Prior Publication Data

US 2012/0165399 A1    Jun. 28, 2012

Related U.S. Application Data

(62) Division of application No. 10/544,066, filed as application No. PCT/IL2004/000108 on Feb. 4, 2004, now Pat. No. 8,338,583.

(60) Provisional application No. 60/444,670, filed on Feb. 4, 2003.

(51) Int. Cl.
```
C12N 15/11     (2006.01)
A61K 48/00     (2006.01)
C07H 21/02     (2006.01)
C07H 21/04     (2006.01)
```
(52) U.S. Cl.
USPC ......... 514/44 A; 536/24.5; 435/6.1; 435/91.1; 435/325; 435/375

(58) Field of Classification Search
USPC ........................................... 536/24.5; 514/44
See application file for complete search history.

(56) References Cited

U.S. PATENT DOCUMENTS

| 6,468,983 B2 | 10/2002 | Silverman et al. |
| 2003/0175772 A1 | 9/2003 | Wang |
| 2006/0079471 A1 | 4/2006 | Michaeli |

FOREIGN PATENT DOCUMENTS

| WO | WO 2004/069148 | 8/2004 |
| WO | WO 2007/030167 | 3/2007 |

OTHER PUBLICATIONS

Zhang et al. (Molecular Biochemical Parasitology, 2000 vol. 107:315-319).*
Notice of Allowance Dated Jun. 28, 2012 From the US Patent and Trademark Office Re.: U.S. Appl. No. 10/544,066.
International Search Report Dated Nov. 15, 2005 From the International Searching Authority Re. Application No. PCT/IL04/00108.
Official Action Dated Apr. 4, 2008 From the US Patent and Trademark Office Re.: U.S. Appl. No. 10/544,066.
Official Action Dated Apr. 24, 2011 From the US Patent and Trademark Office Re.: U.S. Appl. No. 10/544,066.
Official Action Dated Sep. 19, 2011 From the US Patent and Trademark Office Re.: U.S. Appl. No. 10/544,066.
Official Action Dated Jul. 20, 2010 From the US Patent and Trademark Office Re.: U.S. Appl. No. 10/544,066.
Response Dated Jan. 19, 2011 to Official Action of Jul. 20, 2010 From the US Patent and Trademark Office Re.: U.S. Appl. No. 10/544,066.
Response Dated Jun. 27, 2011 to Official Action of Apr. 4, 2011 From the US Patent and Trademark Office Re.: U.S. Appl. No. 10/544,066.

(Continued)

*Primary Examiner* — Terra Cotta Gibbs

(57) ABSTRACT

Polynucleotides and a method suitable for downregulation of small nuclear RNA which can be used to treat diseases associated with activity of small nuclear RNA are provided. Specifically, the present invention can be used to downregulate snoRNA molecules or box H/ACA-containing RNA molecules which are involved in diseases such as cancer.

16 Claims, 10 Drawing Sheets

OTHER PUBLICATIONS

Downward "Science, Medicine, and the Future. RNA Interference", BMJ, 328: 1245-1248, 2004.

Dunbar et al. "The U14 SnoRNA Is Required for 2'-O-Methylation of the Pre-18S rRNA in *Xenopus* Oocytes", RNA, 4: 195-204, 1998.

Gupta et al. "Small Nucleolar RNA Interference in *Trypanosoma brucei*: Mechanism and Utilization for Elucidating the Function of SnoRNAs", Nucleic Acids Research, 38(20): 7236-7247, Jul. 3, 2010.

Hammond et al. "Post-Transcriptional Gene Silencing by Double-Stranded RNA", Nature Reviews: Genetics, 2: 110-119, 2001.

Kedde et al. "Telomerase-Independent Regulation of ATR by Human Telomerase RNA", Journal of Biological Chemistry, 281(52): 40503-40514, Dec. 29, 2006.

Kosciolek et al. "Inhibition of Telomerase Activity in Human Cancer Cells by RNA Interference", Molecular Cancer Therapeutics, 2: 209-216, 2003.

Liang et al. "Small Nucleolar RNA Interference Induced by Antisense or Double-Stranded RNA in Trypanosomatids", Proc. Natl. Acad. Sci. USA, 100(13): 7521-7526, 2003.

Lu et al. "Delivering SiRNA In Vivo for Functional Genomics and Novel Therapeutics", RNA Interference Technology, p. 303-317, 2005.

Paul et al. "Effective Exprssion of Small Interfering RNA in Human Cells", Nature Biotechnology, 20: 505-508, 2002.

Protocol Online "What Is Antisense Phosphorothioate Oligonucleotides?", Current Protocols, Protocol Online, Oct. 14, 2006.

Samarsky et al. "RNAi in Drug Development: Practical Considerations", RNA Interference Technology, p. 384-395, 2005.

Zhang et al. "Antisense Telomerase RNA Induced Human Gastric Cancer Cell Apoptosis", Worl Journal of Gastroenterology, 6(3): 430-432, 2000.

Official Action Dated Mar. 19, 2012 From the US Patent and Trademark Office Re.: U.S. Appl. No. 10/544,066.

\* cited by examiner

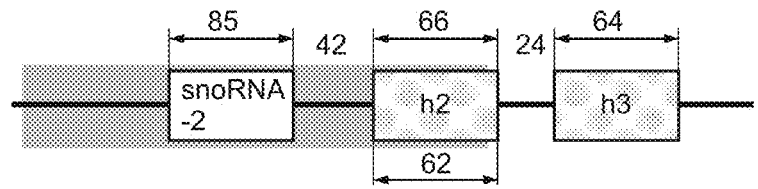
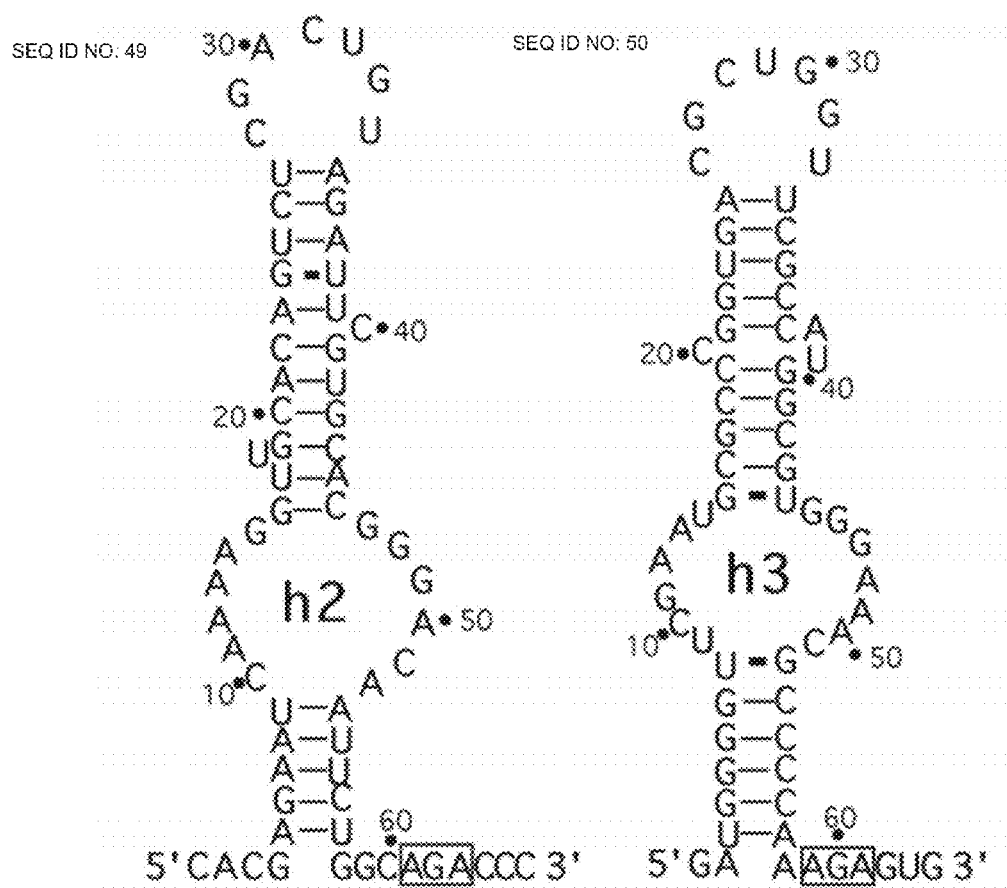
Fig. 5a
Fig. 5b

Human U14 tactatgat gattggttgc cagacattcc cagttccac cagaaatgtt
ttccttatg tggccagtt ctccttgga tgtctgagtg agcatcttca tt    SEQUENCE ID NO.: 47

CCAGACATTCCCAGTTCCACCAG
                     t c  a
                    t     a  a
                    a     g
                    a  g  a
GGTCTGTAAGCGTCAAGGTGGTC

SEQUENCE ID NO.: 48

Fig. 10a

SEQUENCE LISTING

<160> NUMBER OF SEQ ID NOS: 48

<210> SEQ ID NO 1
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 1
catcagatgc cggtagtc                                                 18

<210> SEQ ID NO 2
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 2
caatcttgca cagtgtcg                                                 18

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
acgttctgca atctgaccgc g                                             21

<210> SEQ ID NO 4
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 4
agctatatct ctcgaa                                                   16

<210> SEQ ID NO 5
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 5
gagggaggaa tgaggtgagc                                               20

<210> SEQ ID NO 6
<211> LENGTH: 15
<212> TYPE: DNA
<213> ORGANISM: Artificial sequence
<220> FEATURE:
<223> OTHER INFORMATION: Single strand DNA oligonucleotide

<400> SEQUENCE: 6
cgccgtttgc gttca                                                    15

<210> SEQ ID NO 7
<211> LENGTH: 27
<212> TYPE: DNA

```
<213> ORGANISM: Artificial sequence
<220> FEATURE:
<223> OTHER INFORMATION: Single strand DNA oligonucleotide

<400> SEQUENCE: 7
cgggatcctg ccagaattgt cccgtgc                                27

<210> SEQ ID NO 8
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 8
acagctaccg cgagttgc                                          18

<210> SEQ ID NO 9
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 9
cactctttgg ggcgtttc                                          18

<210> SEQ ID NO 10
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 10
tttcacatgc acgagcatcc                                        20

<210> SEQ ID NO 11
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 11
ttgccggaag acgggttccg ga                                     22

<210> SEQ ID NO 12
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 12
tctygctctc cagtttcrtg                                        20

<210> SEQ ID NO 13
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 13
agcaactcga ggccgt                                            16
```

```
<210> SEQ ID NO 14
<211> LENGTH: 272
<212> TYPE: DNA
<213> ORGANISM: Trypanosoma brucei

<400> SEQUENCE: 14
ccgcgacaag gtcagcctga gggcacacct tcagtgtgtg tacggcctcg ggagggcgta      60
tatccgctcg agtcgcagag cagggaaatg gtggcgtgaa gctctgccac tggtgcatca     120
gtagctcggc attactgtgt tcgatgctct gctctcagtg gacatgatgc tccgccgccc     180
atatatcccg ttatgtatat cctgtgtgcg ctctagttcc gttgggaccc tgaagagtaa     240
gagtaagcac actaaccgtg cattatacat ga                                   272

<210> SEQ ID NO 15
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 15
atagagttca cagttgca                                                    18

<210> SEQ ID NO 16
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 16
aattctcgga ccacgtga                                                    18

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
ccgtcgcaga tggacgttga                                                  20

<210> SEQ ID NO 18
<211> LENGTH: 678
<212> TYPE: DNA
<213> ORGANISM: Leptomonas collosoma

<400> SEQUENCE: 18
aatgatgcac caggctcgcg tttagctgct gactgtcgtg ctgacgcgcc catgcgagct      60
tgcgcgcgtg acgctgtgcg agacatgatt acagatggac aaccgagtca aaaccaaatt    120
attaccgata catccgctga gtacctacgt ccccgtgtc  tgaactccat ggtgtcggct     180
gccgcgcgcg ctgcttggcc tgcgcgcgtc gtgtgttgcg ttgcggcgtg cttgtgcgtc    240
gacgtgcagt tgtgccccgt tttcttcgtg ctgtgttgcc acggctgcaa cgccaggtgc    300
tcaattgatg atgaacgttc tgcaattctg accgcgactg cgcgacgaca aaaccaacga    360
taacatgact accggcatct gatgagcacc tgttgttgtt aatgtgtgtg tgtgtggtgg    420
cgacgctcac gagaatcaaa aggttgcaca gtctcgactg tagattcgtg cacgggacaa    480
ttctggcaga ccccgctgtg tgctgtgttg ctcgtgcgat ggggttcgaa tgcgcccggt    540
```

```
gacgctggtt cgccatggcg tgggaaacgc cccaaagagt gcgagtgcgt gtgcgtgctt    600
gcgggtgcgc ttgcaggtgt gtgtgtgtgt gcgaggcggt gccgatgatt ctacttaatt    660
tctttgctac aggcgatc                                                  678
```

<210> SEQ ID NO 19
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 19

```
cgggatccgc tgcgcgttga catg                                            24
```

<210> SEQ ID NO 20
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 20

```
cgggatccag cggcgtccca cgcagc                                          26
```

<210> SEQ ID NO 21
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 21

```
ccgctcgagt tacctattcc atgcacatt                                       29
```

<210> SEQ ID NO 22
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 22

```
cccaagcttg agaagagtgt gcactaacc                                       29
```

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23

```
tgagacccgc cgacccgaat                                                 20
```

<210> SEQ ID NO 24
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 24

```
cgggatccaa agagagggac gcgaca                                          26
```

<210> SEQ ID NO 25

<211> LENGTH: 1266
<212> TYPE: DNA
<213> ORGANISM: Leptomonas collosoma

<400> SEQUENCE: 25

| | | | | | |
|---|---|---|---|---|---|
| ttgtttctct | ttctctttgt | ttctcttttc | tccgcgtctg | cgtgccgccc | tgcgtgatga | 60 |
| tactgaccct | gctccgctac | tgacatcgtg | aacccatgat | ccgatactct | tcagggcaac | 120 |
| tgacggtgcg | gcatgcgtac | gcgcgctcgc | tcccttgtta | ctcccttgtt | actcccttgt | 180 |
| tactcccttg | ttactccctt | gttgcgttgc | gcgtgcttcg | tctttccgtt | ttctcgcggt | 240 |
| ccgtgctccg | ctgtgtcgcc | cctcccgttc | ttcgctcgcc | ccctgctcg | ctccgcacag | 300 |
| gtggcgcttg | tgctgctcgc | gcgcgtgatg | atccgcgtta | caccaatcga | cactgagtcg | 360 |
| gacccgatgc | tcatgacgca | ccgtgtagcg | accgcggatg | tgctgccgcc | cgtgcggtg | 420 |
| gtgtctgatg | cgcgtgcacg | ccggcctgcg | cgtggcgaca | cgtctgtttt | gtgtgtgtgt | 480 |
| gttgagctgt | gccgcgcgtg | atgatctcgc | aactgagtgt | acctttttcg | attctgcggg | 540 |
| aacgtgaaac | tagcaactcg | cggtagctgt | cgcgtgtgcg | gcggctgcgt | ctgatggcgg | 600 |
| ctgatggctt | ttgtgctgtg | tgttgtgtgt | gttgtgtgtg | ttgtttgtgt | ggttcgtgtg | 660 |
| tgtgcgatgg | cgcgcagccg | aagaaaccag | cgcgagcctg | aaccggtgct | gcgctggtgc | 720 |
| cgacactgtg | caagattgtg | cgtcgtgtgt | gtgcctgtg | cgtgtccttt | gcaacgcgct | 780 |
| attgctctcc | cgatggcttg | tgtttggtgc | ctcgaggaga | tcctgaggcg | cgtgagaacg | 840 |
| gtgcgtgata | ggaagcgcgc | cgaatgtgtg | cgggcgtctg | tgcgcgcgaa | tggaggtgaa | 900 |
| ctacacattc | cgaggtccac | gtggctctgt | ccgtgcctgg | tgagaccttc | tggtagtgtc | 960 |
| gaagatgcgt | gcgttccctc | gtccgcattg | tggagcttcc | tttgtgtgct | gtgtgttgtt | 1020 |
| tgtgcgattt | gtgtgtgtgc | gatggcgcgc | agccgaagaa | accagcgcga | gcctgaaccg | 1080 |
| gtgctgcgct | ggtgccgaca | ctgtgcaaga | ttgtgcgtgc | gtgtgtgtgt | ggctgtgcga | 1140 |
| tgcggttgtg | gcttgtgtaa | gcggacgtaa | ccagccgtgc | gcacgatccg | ttgcgctatt | 1200 |
| cggtcttgtc | gtcgagcaag | agctgctgcc | actggctgcg | gtgctgcggt | gttgcggtgc | 1260 |
| tgcgcg | | | | | 1266 |

<210> SEQ ID NO 26
<211> LENGTH: 863
<212> TYPE: DNA
<213> ORGANISM: Leptomonas collosoma

<400> SEQUENCE: 26

| | | | | | |
|---|---|---|---|---|---|
| ggacgctggg | taaaacacca | cgaaaaaacg | gaaagtgggg | tagctggggt | tcccgagttg | 60 |
| gtcaaagggg | caagacttaa | gttcttgtgc | gcaacgttcg | tgggttcgaa | ccccacctcc | 120 |
| agcatagttt | tccctttccg | ccgactggac | atgtaccatg | aaagtcgcag | cggctgccga | 180 |
| agctctcata | gctcagtcgg | ttagagcgtg | ggtctaataa | gcccaaggtc | acaggttcga | 240 |
| cccctgttgg | gagcactttt | ccaatcgcac | gttttttctt | ttcgcgacgg | gagaaaaagt | 300 |
| cactcctacc | tggactcgaa | ccagggttat | cggattcaga | gtccgaggtg | ataaccgcta | 360 |
| cactatagga | gcgcacgcct | gtgctggcgt | gggcgtagtt | gtacttgcta | attcacaata | 420 |
| ctaagatacg | gaaaacacgt | gtcactgcga | acgttttttc | ctctaagaag | cggagccccct | 480 |
| tcggggggaca | tccacaacct | ggaacttcaa | cagagaagat | tagcactctc | cctgcgcaag | 540 |
| gctgatgtca | atcttcgaga | gatatagctt | ttcgccacgc | tttcctcacg | tgttttccct | 600 |
| tcagtggctt | agaagactag | ttcaccggac | gagagagatg | gagagagaga | gagaagctgc | 660 |

```
cgcacggctt gtgtgcgggt tcccccgccc ccaccctca ctcccaagct caccgcgcac    720
cgttttcggc gcgggggagg gagggtgcg caccgcccga cggcgcccgc cgcgagccct    780 tcccccacg ccccacgcgg ggcaaaccca acccagcacg cgcacaccac cccagggaga    840
ccccgccagg ccccctctat ctt                                          863

<210> SEQ ID NO 27
<211> LENGTH: 1473
<212> TYPE: DNA
<213> ORGANISM: Leptomonas mirabilis

<400> SEQUENCE: 27
gctgtaggtg aacctgcagc tggatcattt tccgatagaa acgatattc aacaagaacc    60 ggggggagc tcctctcccc acgcctctct cttcttccct cttcttttc ttcccttcct   120 ttttccctct ctcgtgacgt cgcccgagac atgcgccctt tccctcatca tcctctctcc   180
ctctccctct ctccgcgctg tgtgtgtgcg tgtgtgtgtg cgaacacatg catgtgatgc   240
acggccggcg gggggggaa gaattggggg ttcgtggggg gttgtgtgtg tggccgggta   300
gacagaacgg gtgtggggtt atatattagg aggggttgtt gaagccagag ggtgtaaaga   360
aggggggggg gtgggaaac aaaggggtt ctcttcccac ttaccttgtg tgttttgggg   420
tgtggcggtg tggcgtgtgt gtcttatact cacacgtcgc gcgtatcccc tcaaagagaa   480
gcacaagcaa ccttcttttg tatacaaagc cttttgccgc ttgacgcgcg cacacacggt   540
cgtcttcaag cacacacaca aacacacgtg cacgcgagtg tgcgtatgtg tgtgtgtgcg   600
agagagaggg cctccgtgtg tatgtgcgtg tggagcacgg ccccaacaac gtgtcgcgat   660
ggatggcttg gcttcctatt tcgttgaaga acgcagtaaa gtgcgataag tggtatcaat   720
tgcagaacca tccaattacc gaatctttga acgcaaacgg gcatgggag aaaccttac    780 gggccatccc cgtgcatgcc atattctcag tgtcgaacaa taaacaaaca tccaccctgt   840
gcgtgtgtgt gcgtgcccct gtgtgtgtgc gcgcgcgtgc ggggtgctgc catgtttgga   900
atctgtaaaa gagagccctt ggagtaggat gaaataaaat aaccaaaata aagatccgct   960
tcggtgcttt tttcggacac cacccacca ccacgcgccc ccgtgcatat ttatatgtac   1020
gcgtgtgtgt gtgtgggcgt gtgggcgtct gacaaacaca acaaacacaa acgaggccc   1080 aaaaactctc cttttgcgtg tgtcgagagc tctctttctc tccctctcc tcttccgcgc   1140 ctccgtgtgt ccttccctct cctctctccc tcctctgccc aactctccct ctcttttccc   1200
tctctcgctc tctctcgtct ctactctcct ctcctccctc tcttcctctc gtccgttttc   1260
tctcgggaga acggcgcgag aggcgggaa gggggggag gggaagagaa gaaagaatag   1320
agagggagga aaagagaag gggcgcgggg cgggcgcgaa ggaagagggg gtgtgtggtg   1380
cgcatgtgtg tgtgtgcgaa gagaagaaac caaaagggag gggaagagag tccccatttt   1440
gtttacagac ctgagtgtgg caggactacc cgc                               1473

<210> SEQ ID NO 28
<211> LENGTH: 66
<212> TYPE: DNA
<213> ORGANISM: Leptomonas collosoma

<400> SEQUENCE: 28
cacgagaatc aaaaggttgc acagtctcga ctgtagattc gtgcacggga caattctggc    60
agaccc                                                              66

<210> SEQ ID NO 29
```

```
<211> LENGTH: 1266
<212> TYPE: DNA
<213> ORGANISM: Leptomonas collosoma

<400> SEQUENCE: 29
ttgtttctct ttctctttgt ttctcttttc tccgcgtctg cgtgccgccc tgcgtgatga      60
tactgaccct gctccgctac tgacatcgtg aacccatgat ccgatactct tcagggcaac     120
tgacggtgcg gcatgcgtac gcgcgctcgc tcccttgtta ctcccttgtt actcccttgt     180
tactcccttg ttactcccct gttgcgttgc gcgtgcttcg tctttccgtt ttctcgcggt     240
ccgtgctccg ctgtgtcgcc cctcccgttc ttcgctcgcc ccctgctcg ctccgcacag      300 gtggcgcttg tgctgctcgc gcgcgtgatg atccgcgtta caccaatcga cactgagtcg     360
gacccgatgc tcatgacgca ccgtgtagcg accgcggatg tgctgccgcc ccgtgcggtg     420
gtgtctgatg cgcgtgcacg ccggcctgcg cgtggcgaca cgtctgtttt gtgtgtgtgt     480
gttgagctgt gccgcgcgtg atgatctcgc aactgagtgt acctttttcg attctgcggg     540
aacgtgaaac tagcaactcg cggtagctgt cgcgtgtgcg gcggctgcgt ctgatggcgg     600
ctgatggctt ttgtgctgtg tgttgtgtgt gttgtgtgtg ttgtttgtgt ggttcgtgtg     660
tgtgcgatgg cgcgcagccg aagaaaccag cgcgagcctg aaccggtgct gcgctggtgc     720
cgacactgtg caagattgtg cgtgcgtgtg tgtgcctgtg cgtgtccttt gcaacgcgct     780
attgctctcc cgatggcttg tgtttggtgc ctcgaggaga tcctgaggcg cgtgagaacg     840
gtgcgtgata ggaagcgcgc cgaatgtgtg cgggcgtctg tgcgcgcgaa tggaggtgaa     900
ctacacattc cgaggtccac gtggctctgt ccgtgcctgg tgagaccttc tggtagtgtc     960
gaagatgcgt gcgttccctc gtccgcattg tggagcttcc tttgtgtgct gtgtgttgtt    1020
tgtgcgattt gtgtgtgtgc gatggcgcgc agccgaagaa accagcgcga gcctgaaccg    1080
gtgctgcgct ggtgccgaca ctgtgcaaga ttgtgcgtgc gtgtgtgtgt ggctgtgcga    1140
tgcggttgtg gcttgtgtaa gcggacgtaa ccagccgtgc gcacgatccg ttgcgctatt    1200
cggtcttgtc gtcgagcaag agctgctgcc actggctgcg gtgctgcggt gttgcggtgc    1260
tgcgcg                                                                1266

<210> SEQ ID NO 30
<211> LENGTH: 65
<212> TYPE: DNA
<213> ORGANISM: Leptomonas collosoma

<400> SEQUENCE: 30
gcgatggggt tcgaatgcgc ccggtgacgc tggttcgcca tggcgtggga acgccccaaa      60
gagtg                                                                   65

<210> SEQ ID NO 31
<211> LENGTH: 1130
<212> TYPE: DNA
<213> ORGANISM: Leptomonas collosoma

<400> SEQUENCE: 31
tgtgcgatgc ggttgtggct tgtgtaagcg gacgtaacca gccgtgcgca cgatccgttg      60
cgctattcgg tcttgtcgtc gagcaagagc tgctgccact ggctgcggtg ctgcggtgtt     120
gcggtgctgc gcgcgcgtgc atgatgagat atacaagctt aggacacctt tggatgctcg     180
tgcatgtgaa aagaacgtct tgcaaacatc gattcgtact ctgacgacgc gacgtgcggc     240
tgtgctgtgg cctgtgcgcg ttgatgcgcg tacctgcgta cctgcgtacc tgcgtacctg     300
```

| | |
|---|---|
| cgtacctgcg tacctgcgta cctgcgtacc tgcgtacctg tgcgtgtgtg tgactgcgct | 360 |
| gcgctatgat gatacatcta tgttacggtc caaacagttt gaatggcatt tcatgtgaat | 420 |
| acaacataac aatcaccttt cggctgagtg cgcagcgtgt gtgtgcgtga gtgcgctggt | 480 |
| tgctgtggaa gcggacttcc ctgggctggt ggctgtccaa tgccctgtat tgtgcccgtg | 540 |
| tacagttccg caagagacga tctgcgctac gaagtggtgt gcgtatgcgc gtcactgtga | 600 |
| gtgtgtgtgt gtgtgtcgcg cgcgtcctct gtgatggaaa gaactttctt tgtgcgcgag | 660 |
| cgcagccatg agcgcacatt tcgagccaaa acaaaactca acaggtctga tgacggacgc | 720 |
| tgcgcgtgtg gttgcttgct gtgcttgctg tgtgtgtgtg tgtgtgcggt gtttgcactg | 780 |
| tgcgtgcagg cgtgccttga gacccgccga cccgaatgat ggacgagcgg gagcatccgc | 840 |
| actccgagac gccgtgcttg tgtggtgctt gtgtggtgtg gtgtgctggc gcgcgcgcat | 900 |
| gatgacaact ctatagtttc ctgtcagcct gataccctct cgtgaagaca taacttcaac | 960 |
| tcagctcaca ctgaagcgct gcgctgccgc tgccgccgga gcgctgctcc actgcgcgtt | 1020 |
| gtcgcgtccc tctctttgtt tctctttctc tttgtttctc ttttctccgc gtctgcgtgc | 1080 |
| cgccctgcgt gatgatactg accctgctcc gctactgaca tcgtgaaacc | 1130 |

<210> SEQ ID NO 32
<211> LENGTH: 2724
<212> TYPE: DNA
<213> ORGANISM: Leishmania tarentolae
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (2173)..(2173)
<223> OTHER INFORMATION: n is a, c, g, or t
<220> FEATURE:
<221> NAME/KEY: misc_feature
<222> LOCATION: (2307)..(2307)
<223> OTHER INFORMATION: n is a, c, g, or t
<220> FEATURE:
<221> NAME/KEY: misc_feature
<222> LOCATION: (2699)..(2700)
<223> OTHER INFORMATION: n is a, c, g, or t
<220> FEATURE:
<221> NAME/KEY: misc_feature
<222> LOCATION: (2708)..(2708)
<223> OTHER INFORMATION: n is a, c, g, or t

<400> SEQUENCE: 32

| | |
|---|---|
| cagctgtgaa gagctccaga agaagaggcg aaccaccacc ctctcatggc cctggcaccc | 60 |
| tccatctgcc gcccaccaac gactcatctc tgcactcgtc attgcctgag gggagagacc | 120 |
| tctgcttggt gcatgtctct cacaccacaa gtacccccct gctttacagc tgaacccact | 180 |
| actccaatcc actttagcac gcccactctt ccgtcttgta gagctccctg accatccatg | 240 |
| ccgtccttcc gaccagacta tgcacgagta acgtgcctca ccctcgactg acccttcgat | 300 |
| cctcatcctc cctttccgct cctgactctt tcaccgcaag tatagagtca ccacagacac | 360 |
| accaccttcc tcactgagag actatatgca ccactctgag gttgcgttcc gcgtgtgcct | 420 |
| gcgtgtgnag ctgtcgatgc gcggaggagg agccgcgagg gtgcgggtgc gtgcggcgca | 480 |
| ccgcgctcac cgagggcggt cgcggcctcc ctcgcggcct ggtgctgcgc cgccgctgtg | 540 |
| acctgtgcac acatgatgat tgactgtaac atcacagact ttgagtcgcg atgatagcaa | 600 |
| ccatgtcgcc ccagtctgac gtggctggcg ccgtgcatgc cgtgtgtgtg tgcgtgcgca | 660 |
| tctagagcta tgcctgtgtg tgattcgcgg gggccgtgcg tgcccgccgc tacgcgttga | 720 |

```
catgatcgac accttggctg atgtaaagcc gtcgcagatg gacgttgagt ggcgcacgcc    780
gtgaaaccaa cccccgcctc gtctgatcgc gcgtactctt tccccctccc cttccttcct    840
accgcgctgc acgagcaagt gcgcgtgtgc agcgtacgtt acgttgcttc tagtgctact    900
gctgtccact ggccccgtca cctcgagggc gcccgtgccg cttgccggcg catgctgggc    960
gtactggcct cgagtcgctg cggcgctggt gcacgtgcgc acgtgcgtgt gccgtctgcg   1020
ctgcgattcg gggggccaca gagcaagggg tgcgagtgcg cggcgtgatg ctcggcgcgc   1080
tcccgcgtgc ctgacgcacc gccggcgcgc gcggttccc gttacgcata tcctgtgtgc   1140
gctccagccc cgtcccccgg atgacgagtc tgcaaccaac catgcgttac acattgcctg   1200
cgcgcgtgcg cgaggagacg acgcgctcac tgtagtgcgc gtgccgcaag acccacaggc   1260
accgtgcatg aaactggagc gctagattgc aagctgccca cggtgcgac ggtgcggggg    1320
gggatgtgag acaacacgac aacaaagcac agtttgaggc tgatgcatcg ctgatcgacc   1380
acttcacacg tgtgagctac ctctgctgac gcaccgctgc cgccttggtg ccgagaccg    1440
gcgcgcccct ccccccctccc ccttcccca caccgctgcg tggcacgcgg ctggcggtgc   1500
gtgcgcagta cgattaaaca cggacgcgcc gctgcatatg cttggtgctg cgccgtccg    1560
ccagtgtcgt acgagatgga gagaggcgag ggcgtgccgg cgctggtgca gtgctgccag   1620
gtaaagtgac gatggtgtgt cccatccgcg ccactggttc aagcggcacg agagcgagtg   1680
acgaggtatg cgcgtgttgc tgctgctgcg atgggggagg cgtgcacggc gacacagaga   1740
gagagagaaa gagagaaagg gcgcggtaga gacgcggacg caggatgcac aaaactgatt   1800
caggcgtgcc gatgcacgcg tcaggaggcc cctgactgag agactatcat gcaccactct   1860
gaggttgcgt tccgcgtgtg cctgcgtgtg agctgtcgat gcgcggagga ggagccgcga   1920
gggtgcgggt gcgtgcggcg caccgcgcct caccgagggc ggtcgcggcc tccctcgcgg   1980
cctggtgctg cgcgcgccgc tgtggacctg tgcacacatg atgattgact gtaacatcac   2040
agactttgag tcgcgatgat agcaaccatg tcgccccagt ctgacgtgcc gtggcgccgt   2100
gcatgccgtg tgtgtgtgcg tgcgcatcta gagctatgcc tgtgtgtaat tcgcgggggc   2160
cgtgcgtgcc cgncctacgc gttgacatga tcgacacctt ggctgatgta aagccgtcgc   2220
agatggacgt tgagtggcgc acgccgtgaa accaaccccg cctcgtctga tcgcgcgtac   2280
tctttcccccc tccccttcct tcctacngge ctgcacgaga agtgcgcgtg tgcagcgtac   2340
gttacgttgc ttctagtgct actgctgtcc actggccccg tcacctcgag ggcgcccgtg   2400
ccgcttgccg cggcatgctg ggcgtacggc ctcgagtcgc tgcggcgctg gtgcacgtgc   2460
gcacgtcggt gtgccgtctg cgctgtgggg ggcgttgtgg tttatatatg ttggagaact   2520
gaaaccggca caagtgcgaa gagtgcgcgg cggcgatgga ggcgaaggac tcgcgtggcg   2580
tcttctgtgg aacgtagaca gtgcgtacgg gaggagcaga aagagaaaca aattgcgcag   2640
tcggttgcag gagtgctgga gggagggagt ggtttgtttt cacagaaaca gctaccggnn   2700
ctaccgtngg cagatgcaat gaga                                          2724
```

<210> SEQ ID NO 33
<211> LENGTH: 72
<212> TYPE: DNA
<213> ORGANISM: Trypanosoma brucei

<400> SEQUENCE: 33

```
aaagctcttt tatgtagtgt gcgtaccacg aaagtagcag gtactgcgac acgaaactgg     60
agagcgagac tc                                                        72
```

<210> SEQ ID NO 34
<211> LENGTH: 1130
<212> TYPE: DNA
<213> ORGANISM: Leptomonas collosoma

<400> SEQUENCE: 34

```
tgtgcgatgc ggttgtggct tgtgtaagcg acgtaaccga gccgtgcgca cgatccgttg      60
cgctattcgg tcttgtcgtc gagcaagagc tgctgccact ggctgcggtg ctgcggtgtt     120
gcggtgctgc gcgcgcgtgc atgatgagat atacaagctt aggacacctt tggatgctcg     180
tgcatgtgaa aagaacgtct tgcaaacatc gattcgtact ctgacgacgc gacgtgcggc     240
tgtgctgtgg cctgtgcgcg ttgatgcgcg tacctgcgta cctgcgtacc tgcgtacctg     300
cgtacctgcg tacctgcgta cctgcgtacc tgcgtacctg tgcgtgtgtg tgactgcgct     360
gcgctatgat gatacatcta tgttacggtc caaacagttt gaatggcatt tcatgtgaat     420
acaacataac aatcaccttt cggctgagtg cgcagcgtgt gtgtgcgtga gtgcgctggt     480
tgctgtggaa gcggacttcc ctgggctggt ggctgtccaa tgccctgtat tgtgcccgtg     540
tacagttccg caagagacga tctgcgctac gaagtggtgt gcgtatgcgc gtcactgtga     600
gtgtgtgtgt gtgtgtcgcg cgcgtcctct gtgatggaaa gaactttctt tgtgcgcgag     660
cgcagccatg agcgcacatt tcgagccaaa acaaaactca acaggtctga tgacggacgc     720
tgcgcgtgtg gttgcttgct gtgcttgctg tgtgtgtgtg tgtgtgcggt gtttgcactg     780
tgcgtgcagg cgtgccttga gacccgccga cccgaatgat ggacgagcgg gagcatccgc     840
actccgagac gccgtgcttg tgtggtgctt gtgtggtgtg gtgtgctggc gcgcgcgcat     900
gatgacaact ctatagtttc ctgtcagcct gataccctct cgtgaagaca taacttcaac     960
tcagctcaca ctgaagcgct gcgctgccgc tgccgccgga gcgctgctcc actgcgcgtt    1020
gtcgcgtccc tctctttgtt tctctttctc tttgtttctc ttttctccgc gtctgcgtgc    1080
cgccctgcgt gatgatactg accctgctcc gctactgaca tcgtgaaacc                1130
```

<210> SEQ ID NO 35
<211> LENGTH: 95
<212> TYPE: DNA
<213> ORGANISM: Trypanosoma brucei

<400> SEQUENCE: 35

```
cactgatgaa agagcttccg ataccgcgta ggcggaacgg aaacacacta tgtcgatgca      60
actgtgaact ctatctttcg ctccgagctg acgtg                                 95
```

<210> SEQ ID NO 36
<211> LENGTH: 77
<212> TYPE: DNA
<213> ORGANISM: Trypanosoma brucei

<400> SEQUENCE: 36

```
ggaaggccca cattggagtt gtgtcttggg ctaacatttc tgtgtccttg tttgcacact      60
cacgtggtcc gagaatt                                                     77
```

<210> SEQ ID NO 37
<211> LENGTH: 92
<212> TYPE: DNA
<213> ORGANISM: Trypanosoma brucei

<400> SEQUENCE: 37

```
gaagtgattg acacctaggc cgatgtaaag ccgtcgcaga tggacgttga tatcttgtga      60
```

| | |
|---|---:|
| aaacagtact attttatgcc ctgactgatc gc | 92 |

<210> SEQ ID NO 38
<211> LENGTH: 2724
<212> TYPE: DNA
<213> ORGANISM: Leishmania tarentolae
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (2173)..(2173)
<223> OTHER INFORMATION: n is a, c, g, or t
<220> FEATURE:
<221> NAME/KEY: misc_feature
<222> LOCATION: (2307)..(2307)
<223> OTHER INFORMATION: n is a, c, g, or t
<220> FEATURE:
<221> NAME/KEY: misc_feature
<222> LOCATION: (2699)..(2700)
<223> OTHER INFORMATION: n is a, c, g, or t
<220> FEATURE:
<221> NAME/KEY: misc_feature
<222> LOCATION: (2708)..(2708)
<223> OTHER INFORMATION: n is a, c, g, or t

<400> SEQUENCE: 38

| | |
|---|---:|
| cagctgtgaa gagctccaga agaagaggcg aaccaccacc ctctcatggc cctggcaccc | 60 |
| tccatctgcc gcccaccaac gactcatctc tgcactcgtc attgcctgag gggagagacc | 120 |
| tctgcttggt gcatgtctct cacaccacaa gtacccccct gctttacagc tgaacccact | 180 |
| actccaatcc actttagcac gcccactctt ccgtcttgta gagctccctg accatccatg | 240 |
| ccgtccttcc gaccagacta tgcacgagta acgtgcctca ccctcgactg acccttcgat | 300 |
| cctcatcctc cctttccgct cctgactctt tcaccgcaag tatagagtca ccacagacac | 360 |
| accaccttcc tcactgagag actatatgca ccactctgag gttgcgttcc gcgtgtgcct | 420 |
| gcgtgtgnag ctgtcgatgc gcggaggagg agccgcgagg gtgcgggtgc gtgcggcgca | 480 |
| ccgcgctcac cgagggcggt cgcggcctcc ctcgcggcct ggtgctgcgc cgccgctgtg | 540 |
| acctgtgcac acatgatgat tgactgtaac atcacagact ttgagtcgcg atgatagcaa | 600 |
| ccatgtcgcc ccagtctgac gtggctggcg ccgtgcatgc cgtgtgtgtg tgcgtgcgca | 660 |
| tctagagcta tgcctgtgtg tgattcgcgg gggccgtgcg tgcccgccgc tacgcgttga | 720 |
| catgatcgac accttggctg atgtaaagcc gtcgcagatg gacgttgagt ggcgcacgcc | 780 |
| gtgaaaccaa ccccgcctc gtctgatcgc gcgtactctt tcccccctccc cttccttcct | 840 |
| accgcgctgc acgagcaagt gcgcgtgtgc agcgtacgtt acgttgcttc tagtgctact | 900 |
| gctgtccact ggccccgtca cctcgagggc gcccgtgccg cttgccggcg catgctgggc | 960 |
| gtactggcct cgagtcgctg cggcgctggt gcacgtgcgc acgtgcgtgt gccgtctgcg | 1020 |
| ctgcgattcg gggggccaca gagcaagggg tgcgagtgcg cggcgtgatg ctcggcgcgc | 1080 |
| tcccgcgtgc ctgacgcacc gccggcgcgc cgcggttccc gttacgcata tcctgtgtgc | 1140 |
| gctccagccc cgtcccccgg atgacgagtc tgcaaccaac catgcgttac acattgcctg | 1200 |
| cgcgcgtgcg cgaggagacg acgcgctcac tgtagtgcgc gtgccgcaag acccacaggc | 1260 |
| accgtgcatg aaactggagc gctagattgc aagctgccca gcggtgcgac ggtgcggggg | 1320 |
| gggatgtgag acaacacgac aacaaagcac agtttgaggc tgatgcatcg ctgatcgacc | 1380 |
| acttcacacg tgtgagctac ctctgctgac gcaccgctgc cgccttggtg gccgagaccg | 1440 |
| gcgcgcccct cccccctccc cccttcccca caccgctgcg tggcacgcgg ctggcggtgc | 1500 |

```
gtgcgcagta cgattaaaca cggacgcgcc gctgcatatg cttggtgctg cgccgtccg    1560 ccagtgtcgt acgagatgga gagaggcgag ggcgtgccgg cgctggtgca gtgctgccag    1620
gtaaagtgac gatggtgtgt cccatccgcg ccactggttc aagcggcacg agagcgagtg    1680
acgaggtatg cgcgtgttgc tgctgctgcg atggggcagg cgtgcacggc gacacagaga    1740
gagagagaaa gagagaaagg gcgcggtaga gacgcggacg caggatgcac aaaactgatt    1800
caggcgtgcc gatgcacgcg tcaggaggcc cctgactgag agactatcat gcaccactct    1860
gaggttgcgt tccgcgtgtg cctgcgtgtg agctgtcgat gcgcggagga ggagccgcga    1920
gggtgcgggt gcgtgcggcg caccgcgcct caccgagggc ggtcgcggcc tccctcgcgg    1980
cctggtgctg cgcgcgccgc tgtggacctg tgcacacatg atgattgact gtaacatcac    2040
agactttgag tcgcgatgat agcaaccatg tcgccccagt ctgacgtgcc gtggcgccgt    2100
gcatgccgtg tgtgtgtgcg tgcgcatcta gagctatgcc tgtgtgtaat tcgcggggc    2160 cgtgcgtgcc cgncctacgc gttgacatga tcgacaccttggctgatgta aagccgtcgc    2220 agatggacgt tgagtggcgc acgccgtgaa accaaccccg cctcgtctga tcgcgcgtac    2280
tctttccccc tccccttcct tcctacnggc ctgcacgaga agtgcgcgtg tgcagcgtac    2340
gttacgttgc ttctagtgct actgctgtcc actggccccg tcacctcgag ggcgcccgtg    2400
ccgcttgccg cggcatgctg ggcgtacggc ctcgagtcgc tgcggcgctg gtgcacgtgc    2460
gcacgtcggt gtgccgtctg cgctgtgggg ggcgttgtgg tttatatatg ttggagaact    2520
gaaaccggca caagtgcgaa gagtgcgcgg cggcgatgga ggcgaaggac tcgcgtggcg    2580
tcttctgtgg aacgtagaca gtgcgtacgg gaggagcaga aagagaaaca aattgcgcag    2640
tcggttgcag gagtgctgga gggagggagt ggtttgtttt cacagaaaca gctaccggnn    2700
ctaccgtngg cagatgcaat gaga                                          2724
```

<210> SEQ ID NO 39
<211> LENGTH: 804
<212> TYPE: DNA
<213> ORGANISM: Artificial sequence
<220> FEATURE:
<223> OTHER INFORMATION: pX expression vector, neo/hygro resistance gene

<400> SEQUENCE: 39

```
atgggatcgg ccattgaaca agatggattg cacgcaggtt ctccggccgc ttgggtggag     60
aggctattcg gctatgactg ggcacaacag acaatcggct gctctgatgc cgccgtgttc    120
cggctgtcag cgcaggggcg cccggttctt tttgtcaaga ccgacctgtc cggtgccctg    180
aatgaactgc aggacgaggc agcgcggcta tcgtggctgg ccacgacggg cgttccttgc    240
gcagctgtgc tcgacgttgt cactgaagcg ggaagggact ggctgctatt gggcgaagtg    300
ccggggcagg atctcctgtc atctcacctt gctcctgccg agaaagtatc catcatggct    360
gatgcaatgc ggcggctgca tacgcttgat ccggctacct gcccattcga ccaccaagcg    420
aaacatcgca tcgagcgagc acgtactcgg atggaagccg gtcttgtcga tcaggatgat    480
ctggacgaag agcatcaggg gctcgcgcca gccgaactgt tcgccaggct caaggcgcgc    540
atgcccgacg gcgaggatct cgtcgtgacc catggcgatg cctgcttgcc gaatatcatg    600
gtggaaaatg gccgcttttc tggattcatc gactgtggcc ggctgggtgt ggcggaccgc    660
tatcaggaca tagcgttggc taccgtgat attgctgaag agcttggcgg cgaatgggct    720
gaccgcttcc tcgtgcttta cggtatcgcc gctcccgatt cgcagcgcat cgccttctat    780
cgccttcttg acgagttctt ctga                                          804
```

```
<210> SEQ ID NO 40
<211> LENGTH: 397
<212> TYPE: DNA
<213> ORGANISM: Mus musculus

<400> SEQUENCE: 40
acctaaccct gattttcatt agctgtgggt tctggtcttt tgttctccgc ccgctgtttt      60
tctcgctgac ttccagcggg ccaggaaagt ccagacctgc agcgggccac cgcgcgttcc     120
cgagcctcaa aaacaaacgt cagcgcagga gctccaggtt cgccgggagc tccgcggcgc     180
cgggccgccc agtcccgtac ccgcctacag gccgcggccg gctgggtc ttaggactcc       240 gctgccgccg cgaagagctc gcctctgtca gccgcggggc gccggggct ggggccaggc      300 cgggcgagcg ccgcgaggac aggaatggaa ctggtccccg tgttcggtgt cttacctgag     360
ctgtgggaag tgcacccgga actcggttct cacaacc                             397

<210> SEQ ID NO 41
<211> LENGTH: 451
<212> TYPE: DNA
<213> ORGANISM: Homo sapiens

<400> SEQUENCE: 41
gggttgcgga gggtgggcct ggagggggtg gtggccattt tttgtctaac cctaactgag      60
aagggcgtag gcgccgtgct tttgctcccc gcgcgctgtt tttctcgctg actttcagcg     120
ggcggaaaag cctcggcctg ccgccttcca ccgttcattc tagagcaaac aaaaaatgtc     180
agctgctggc ccgttcgccc ctcccgggga cctgcggcgg gtcgcctgcc agcccccga     240 accccgcctg gaggccgcgg tcggcccggg gcttctccgg aggcacccac tgccaccgcg     300
aagagttggg ctctgtcagc cgcgggtctc tcggggcga gggcgaggtt caggcctttc      360
aggccgcagg aagaggaacg gagcgagtcc ccgcgcgcgg cgcgattccc tgagctgtgg     420
gacgtgcacc caggactcgg ctcacacatg c                                   451

<210> SEQ ID NO 42
<211> LENGTH: 92
<212> TYPE: DNA
<213> ORGANISM: Homo sapiens

<400> SEQUENCE: 42
tcactatgat gattggttgc cagacattcg cagtttccac cagaaatgtt tttccttatg      60
ttggccagtt cttccttgga tgtctgagtg ag                                    92

<210> SEQ ID NO 43
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 43
ccagacattc gcagtttcca ccag                                             24

<210> SEQ ID NO 44
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 44
```

-continued

```
ttccaccagt ctcttgaa                                                   18

<210> SEQ ID NO 45
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 45
agcgcgaacg cagtcccc                                                   18

<210> SEQ ID NO 46
<211> LENGTH: 21
<212> TYPE: RNA
<213> ORGANISM: Artificial sequence
<220> FEATURE:
<223> OTHER INFORMATION: SiRNA oligonucleotide targeting human
      telomerase RNA

<400> SEQUENCE: 46
gucuaacccu aacugagaag g                                               21

<210> SEQ ID NO 47
<211> LENGTH: 102
<212> TYPE: DNA
<213> ORGANISM: Homo sapiens
<220> FEATURE:
<221> NAME/KEY: misc_feature
<223> OTHER INFORMATION: U14 snoRNA

<400> SEQUENCE: 47
tcactatgat gattggttgc cagacattcg cagtttccac cagaaatgtt tttccttatg     60
ttggccagtt cttccttgga tgtctgagtg agcatcttca tt                       102

<210> SEQ ID NO 48
<211> LENGTH: 57
<212> TYPE: DNA
<213> ORGANISM: Artificial sequence
<220> FEATURE:
<223> OTHER INFORMATION: pSuper-RETRO expressed ShRNA targeting human
      U14

<400> SEQUENCE: 48
ccagacattc gcagtttcca ccagttcaag agactggtgg aaactgcgaa tgtctgg        57
```

SNORNAI-SMALL NUCLEOLAR RNA DEGRADATION BY RNA INTERFERENCE IN TRYPANOSOMATIDS

RELATED APPLICATIONS

This application is a division of U.S. patent application Ser. No. 10/544,066 filed on Aug. 2, 2005, now U.S. Pat. No. 8,338,583, which is a National Phase of PCT Patent Application No. PCT/IL2004/000108 having International Filing Date of Feb. 4, 2004, which claims the benefit of priority of U.S. Provisional Patent Application No. 60/444,670 filed on Feb. 4, 2003. The contents of all of the above applications are incorporated by reference as if fully set forth herein.

FIELD AND BACKGROUND OF THE INVENTION

The present invention relates to snoRNA specific siRNAs capable of downregulating snoRNAs in the nucleolus or the nucleoplasm and, more particularly, to the use of these snoRNA-siRNAs as silencing agents to target nuclear or nucleolar RNA molecules, such as the telomerase RNA.

Small Nucleolar RNAs (snoRNAs)

Numerous families of small RNAs have been discovered, including small nucleoplasmic RNAs (snRNAs) and small nucleolar RNAs (snoRNAs). These small RNA molecules function in mRNA splicing (U1, U2, and U4 to U6 snRNAs), mRNA and rRNA processing (U7 snRNA; U3 and U8 snoRNAs), and site selection for RNA modification by methylation of the 2' hydroxyl group (box C/D snoRNAs) or by pseudouridine formation (box H/ACA snoRNAs).

The Box H/ACA snoRNAs

The box H/ACA snoRNAs include an ACA trinucleotide sequence located 3-nucleotides upstream of the mature snoRNA 3' end and a consensus H box sequence (5'-ANANNA-3'), but no other primary sequence identity. Despite this lack of primary sequence conservation, the H and ACA boxes are embedded in an evolutionarily conserved hairpin-hinge-hairpin-tail core secondary structure with the H box in the single-stranded hinge region and the ACA box in the single-stranded tail (Balakin, A., et al., 1996. The RNA world of the nucleolus: two major families of small RNAs defined by different box elements with related functions. Cell 86: 823-834; Ganot, P., et al., 1997. The family of box ACA small nucleolar RNAs is defined by an evolutionarily conserved secondary structure and ubiquitous sequence elements essential for RNA accumulation. Genes Dev. 11: 941-956). Although box H/ACA snoRNAs are associated with higher-order nucleolar structures, little is known about the composition of the presumed box H/ACA snoRNA particles (snoRNPs). Two *S. cerevisiae* proteins, Gar1p and Cbf5p, have been shown to associate specifically with box H/ACA snoRNAs (Bousquet-Antonelli, C., et al., 1997. A small nucleolar RNP protein is required for pseudouridylation of eukaryotic ribosomal RNAs. EMBO J. 16: 4770-4776). Of these two, only Cbf5p, a putative pseudouridine synthase, is required for H/ACA snoRNA stability (Lafontaine, D. L. et al., 1998. The box H+ACA snoRNAs carry Cbf5p, the putative rRNA pseudouridine synthase. Genes Dev. 12: 527-537).

The Box C/D snoRNAs

The box C/D snoRNAs contain two sequence motifs, box C (RUGAUGA, where R is any purine) and box D (CUGA), which are located only a few nucleotides away from the 5' and 3' ends, respectively, and generally brought into close proximity by base pairing of the four or five terminal nucleotides. This characteristic 5'-3' terminal stem-box C/D structure plays a critical role in the control of snoRNA biogenesis and nucleolar localization. C/D box snoRNAs also contain, immediately upstream from box D or from another CUGA motif (box D') in their 5' half, 10- to 21-nucleotide regions complementary to rRNA, thereby spanning sites of 2'-O-methylation. In the corresponding snoRNA-rRNA duplex, the 2'-O-ribose methylation is directed to the rRNA nucleotide paired to the fifth snoRNA nucleotide upstream from box D or box D' (i.e., the +5 rule).

Involvement of snoRNAs in Regulation of Brain Proteins

The range of action of C/D box methylation guide snoRNAs was found to exceed beyond the field of ribosome biogenesis. For example, the brain-specific C/D box snoRNA HBII-52 was found to contain an 18-nucleotide sequence which exhibits a phylogenetically conserved complementarity to a critical segment of serotonin 2C receptor mRNA, pointing to a potential role in the processing of this mRNA. In addition, this snoRNA, together with the HBII-85 snoRNA, although expressed in the brain, were found to be absent from the brains of Prader-Willi (PWS) patients or PWS mouse model, demonstrating a paternal imprinting status (Cavaillé, J. et al., 2000. Identification of brain-specific and imprinted small nucleolar RNA genes exhibiting an unusual genomic organization. Proc. Natl. Acad. Sci. USA. 97: 14311-14316). Moreover, the location of these snoRNAs genes on the PWS-Angelman syndrome (AS) locus at chromosome 15q11-13, may suggest that snoRNA host-genes and even snoRNA themselves may play a role in imprinting. However, since the snoRNAs are located in the nucleolus, there is no easy way to decipher the function of such RNAs in these diseases.

Telomere Replication Involves the Action of Telomerase

The ends of chromosomes have specialized sequences, termed telomeres, comprising tandem repeats of simple DNA sequences. The telomeres protect the chromosomes from fusion, recombination and degradation (McEachern, M J, et al., 2000. Telomeres and their control. Annu. Rev. Genet. 34: 331-358). Due to the discontinuous mode of DNA replication, the normal replication apparatus fails to complete the replication of the DNA at the telomere. Thus, the extension of the telomeric single-stranded 3' overhangs is catalyzed by a telomerase. Telomerase is a ribonucleoprotein (RNP) enzyme that synthesizes one strand of the telomeric DNA using as a template a sequence contained within the RNA component of the enzyme, designated, the telomerase RNA (TER). The TER subunit of telomerase is comprised of a short sequence which serves as a template for the synthesis of G-rich telomeric repeats and a conserved secondary structure feature that plays essential roles in telomerase assembly and catalytic activity in the nucleolus (Chen, J L, et al., 2000. Secondary structure of vertebrate telomerase RNA. Cell 100: 503-514).

Telomerase RNA Includes an H/ACA snoRNA Domain

The mature human and mouse telomerase RNAs are transcripts of 451 and 397 nucleotides, respectively, including, at the 3' end, a domain which is remarkably similar in its sequence, structure and function to the snoRNA H/ACA domain (Mitchell, J. R., et al., 1999. A box H/ACA small nucleolar RNA-like domain at the human telomerase RNA 3' end. Molecular and Cellular Biology, 19: 567-576). The H/ACA domain confers functional localization of vertebrate telomerase RNAs to the nucleus, the compartment where telomeres are synthesized (Lukowiak A A, et al., 2001. The snoRNA domain of vertebrate telomerase RNA functions to localize the RNA within the nucleus. RNA 7: 1833-44).

Telomere Shortening and Chromosomal Instability

In the absence of telomerase activity, telomeres are shortened by 50-200 nucleotides following each round of chromosome replication (Hastie, N D, et al., 1990. Telomere reduction in human colorectal carcinoma and with ageing. Nature 346: 866-868). Thus, the telomerase replenishes preexisting telomeres and confers their stability. In addition, the telomerase also catalyzes the de novo synthesis of telomeres by the addition of telomeric sequences to chromosome breakpoints that do not end with telomeric repeats.

Telomere shortening has been documented in vivo as a function of human age. However, several human diseases were found to be related to increased telomere shortening and instability. For example, patients suffering from dyskeratosis congenita (DKC) exhibit defects in highly regenerative tissues such as skin and bone marrow, chromosome instability and a predisposition to develop certain types of malignancies. The X-linked form of DKC is caused by mutations in a gene encoding a putative pseudouridine synthase, dyskerin. Dyskerin is associated with H/ACA snoRNAs and with human telomerase RNA. Primary cell lines from DKC-affected males exhibit up to 50% reduction in the human telomerase RNA (hTER) steady state and reduced levels of telomerase activity, suggesting that compromised telomerase function involves in the pathology of the disease (Mitchell, J R, et al., 1999. A telomerase component is defective in the human disease dyskeratosis congenita. Nature 402: 551-555). In addition, the very rare autosomal dominant form of DKC is caused by mutations in the telomerase RNA component (TERC) gene leading to very short telomeres in such patients (Vulliamy, T. et al., 2001. The RNA component of telomerase is mutated in autosomal dominant dyskeratosis congenita. Nature 413: 432-435). Moreover, mutations in the TERC gene were also found in patients with idiopathic aplastic anemia and in patients with constitutional aplastic anemia (Vulliamy, T., et al., 2002. Association between aplastic anaemia and mutations in telomerase RNA. Lancet 359: 2168-2170).

Inhibition of Telomerase as Cancer Therapy

Human cell transformation is correlated with the activation of telomerase and telomere stabilization. Thus, it was found that telomerase is activated by the MYC oncogene and that human telomerase reverse transcriptase (hTERT) is involved in cell immortalization via the human Papilloma virus E7 oncogene (Greider, C W. 1999. Telomerase activation. One step on the road to cancer? Trends Genet. 15: 109-112). In addition, the majority of tumors contain active telomerase, whereas most normal cells do not. Moreover, a telomerase knockout mouse has established a link between telomere attrition and chromosomal instability characteristics of human hepatocellular carcinoma (Farazi, P A, et al., 2003. Differential impact of telomere dysfunction on initiation and progression of hepatocellular carcinoma. Cancer Res. 63: 5021-5027).

Thus, inhibition of telomerase activity in tumor cells would lead to telomere shortening and prevention of cancer progression. Therefore, the development of telomerase inhibitors may provide the rational for cancer therapy.

Indeed, several prior art studies have attempted to inhibit telomerase activity. A thio-phosphoramidate oligonucleotide targeted against the telomerase RNA was found to inhibit the cytokine-induced telomerase activity and to induce a progressive telomere shortening [Akiyama, M, et al., 2003. Effects of oligonucleotide N3'→EP5' thio-phosphoramidate (GRN163) targeting telomerase RNA in human multiple myeloma cells. Cancer Res. 63: 6187-6194]. Most recently, a study utilized short siRNAs was able to demonstrate a modest dose-dependent reduction in telomerase activity. In addition, in the same study, transfection of HeLa cells with a plasmid carrying the hTER gene in the sense and anti-sense orientation resulted in silencing of the telomerase RNA (Kosciolek, B A, et al., 2003 Inhibition of telomerase activity in human cancer cells by RNA interference. Mol. Cancer Ther. 2: 209-216). However, these studies resulted in modest inhibition of the telomerase activity. In addition, the use of vectors containing relatively long dsRNA in transfections was most likely involved in inhibition of protein synthesis via the activation of protein kinase R (PKR) and the inactivation of eIF2a.

There is thus a widely recognized need for, and it would be highly advantageous to have, a method of downregulating in general and snoRNA in particular devoid of the above limitations.

While reducing the present invention to practice, the present inventors have found that siRNA targeted against snoRNA molecules can silence nuclear and nucleolar RNA molecules containing the box C/D or box H/ACA domains. Thus, the present inventor has generated a method of treating snoRNA-related disorders.

SUMMARY OF THE INVENTION

According to one aspect of the present invention there is provided an isolated polynucleotide comprising a nucleic acid sequence selected suitable for inducing RNAi-mediated degradation of a small nuclear RNA.

According to another aspect of the present invention there is provided a nucleic acid construct capable of expressing the isolated polynucleotide in a cell.

According to yet another aspect of the present invention there is provided a pharmaceutical composition comprising the isolated small nuclear RNA polynucleotide and a pharmaceutically acceptable carrier.

According to still another aspect of the present invention there is provided a method of downregulating a level of small nuclear RNA in a cell, the method comprising providing to the cell a polynucleotide having a nucleic acid sequence selected suitable for inducing RNAi-mediated degradation of the small nuclear RNA thereby downregulating the level of the small nuclear RNA in the cell.

According to an additional aspect of the present invention there is provided a method of treating a disease characterized by abnormal expression or activity of a biomolecule, wherein the biomolecule includes, associates with, synthesized via or modified by a small nuclear RNA, the method comprising providing to cells of an individual having the disease a polynucleotide having a nucleic acid sequence selected suitable for inducing RNAi-mediated degradation of the small nuclear RNA, thereby downregulating the level of the small nuclear RNA in the cells and treating the disease.

According to further features in preferred embodiments of the invention described below, the small nuclear RNA is a snoRNA.

According to still further features in the described preferred embodiments the small nuclear RNA is a box C/D-containing RNA, and/or a box H/ACA-containing RNA.

According to still further features in the described preferred embodiments the nucleic acid sequence contains a sequence at least 75% identical to the polynucleotide set forth by SEQ ID NO:14, 18, 29, 31, 34, 37, 38, or 42 as determined using the BlastN software of the National Center of Biotechnology Information (NCBI) using default parameters.

According to still further features in the described preferred embodiments the nucleic acid sequence contains a sequence at least 75% identical to the polynucleotide set forth by SEQ ID NO:25, 28, 30, 32, 33, or 36 as determined using the BlastN software of the National Center of Biotechnology Information (NCBI) using default parameters.

According to still further features in the described preferred embodiments the snoRNA is selected from the group consisting of U3 snoRNA, U8 snoRNA, snoRNA-2, h1 snoRNA, H2 snoRNA, B5 C/D snoRNA, h3 snoRNA, B2 snoRNA, SLA1 RNA, snoRNA 270, TBC4 snoRNA, TBH1 snoRNA, snoRNA 92, G2 snoRNA, U14 snoRNA, HBII-52 snoRNA, and HBII-85 snoRNA.

According to still further features in the described preferred embodiments the box H/ACA-containing RNA is selected from the group consisting of mouse TER and human TER.

According to still further features in the described preferred embodiments the nucleic acid sequence is double stranded and includes at least 15 and no more than 30 nucleic acids.

According to still further features in the described preferred embodiments the nucleic acid construct further comprising a selection marker gene.

According to still further features in the described preferred embodiments the isolated polynucleotide is expressed in a reverse orientation to the selection marker gene.

According to still further features in the described preferred embodiments the nucleic acid construct includes two promoters flanking the isolated polynucleotide, whereas each promoter is capable of directing transcription of a specific strand of the isolated polynucleotide in the cell.

According to still further features in the described preferred embodiments each promoter is independently selected from the group consisting of T7 promoter, SP6 promoter, T3 promoter, CMV promoter, SV40 promoter, adenovirus major late promoter, Rous sarcoma virus promoter.

According to still further features in the described preferred embodiments providing is effected by introducing into the cell a nucleic acid construct capable of expressing the polynucleotide.

According to still further features in the described preferred embodiments providing is effected by administering to the cell the double stranded nucleic acid sequence.

The present invention successfully addresses the shortcomings of the presently known configurations by providing a method of downregulating small nuclear RNA.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a is a schematic presentation depicting the structure of the snoRNA-2 constructs (58-1 and 58-2). The direction of transcription of the snoRNA-2 or the neo gene are marked with arrows. FIG. 1b illustrates primer extension analysis on RNA derived from cell lines carrying the snoRNA-2 gene in the two orientations. Primer extension analysis was performed using the 43362 (SEQ ID NO:2) and 16865 (SEQ ID NO:1) oligonucleotides which are specific for the h1-snoRNA (SEQ ID NO:25) and snoRNA-2 (SEQ ID NO:18) genes, respectively. Lane 1—wild type; lane 2—snoRNA-2 is in the same orientation as the neo gene; lane 3—snoRNA-2 is in the opposite orientation of the neo gene. The extension products are marked with arrows. The h1-snoRNA primer extension product was used as a measure of the level of RNA in each sample.

FIG. 2a—illustrates the effect of increasing concentrations of G418 on the tagged and wild-type (WT) snoRNA-2 transcripts. FIG. 2b—illustrates the effect of increasing concentrations of G418 on the neo transcript. Note the presence of multiple extension products using the neo primer representing heterogeneity in the 5' cap nucleotides of the neo transcript; FIG. 2c—illustrates the effect of increasing concentrations of G418 on the snoRNA-2 antisense transcript. Primer extension analysis using the h1-snoRNA was used as an internal control for the amount of total RNA used in each sample (FIGS. 2a-b).

FIG. 3a is an RNase protection assay using tagged and wild-type RNA and sense and antisense RNA probes. Tagged RNA was obtained from cells transfected with the snoRNA-2 gene in the opposite direction to the neo gene (i.e., antisense direction) and selected using 600 µg/ml G418. Lane 1—wild-type RNA with labeled antisense RNA probe; lane 2—tagged RNA with labeled antisense RNA probe; lane 3-wild-type RNA with labeled sense RNA probe; lane 4—tagged RNA with labeled sense RNA probe. Shown are the protected fragments obtained using the sense probe (FIG. 3a, marked with asterisks) and the 21-25 siRNA molecules in the tagged RNA obtained using both the sense and antisense probes. M=size marker (pBR322 DNA digested with MspI). Nt=nucleotides. FIG. 3b is a schematic presentation of the template used for synthesizing the sense and anti-sense probes. FIG. 3c depicts the expression pattern of snoRNA-2 in the presence of increasing concentrations of G418. Wild-type cells and cells transfected with the snoRNA-2 gene in the antisense direction (i.e., silenced cells) were selected in the presence of increasing concentrations of G418 and total RNA was subjected to Northern blot hybridization using the snoRNA-2 antisense RNA probe. Lane 1—wild type cells; lane 2—silenced cells selected using 50 µg/ml G418; lane 3—silenced cells selected using 200 µg/ml G418, lane 4—silenced cells selected using 600 µg/ml G418. Note the presence of the low molecular weight RNA (about 25 nucleotides) corresponding to siRNAs in the silenced cells selected in the presence of 600 μg/ml G418 (marked with an open arrow). M=size marker (pBR322 DNA digested with MspI).

FIG. 4a—illustrates the presence of snoRNA-2 siRNAs as revealed using the snoRNA-2 antisense RNA probe. Note the presence of siRNAs (FIG. 4a, marked with an arrow) in both nuclear (FIG. 4a, lane marked with "N") and cytoplasmic (FIG. 4a, lane marked with "C") fractions; M=size marker (pBR322 DNA digested with MspI). FIG. 4b illustrates the expression of U6 snRNA as revealed using the 12407 oligonucleotides probe (SEQ ID NO:4). Note the significant expression level of U6 snRNA in the nuclear fraction (FIG. 4b, lane marked with "N") and the moderate expression level in the cytoplasmic fraction (FIG. 4b, lane marked with "C") fraction. FIG. 4c illustrates the expression of h1 snRNA as revealed using the 43362 oligonucleotide probe (SEQ ID NO:2). Note the presence of h1 snoRNA in the nuclear fraction (FIG. 4c, lane marked with "N") and its absence from the cytoplasmic fraction (FIG. 4c, lane marked with "C"). FIG. 4d illustrates the expression of 5.8S rRNA as revealed using the 19796 oligonucleotide probe (SEQ ID NO:6). Note the significant level of 5.8S rRNA in the cytoplasmic fraction (FIG. 4d, lane marked with "C") and the moderate level of expression of the 5.8S rRNA in the nuclear fraction (FIG. 4d, lane marked with "N").

FIGS. 5a-d illustrates the identification of two novel H/ACA-like RNAs in the snoRNA-2 locus. FIG. 5a is a schematic presentation of the snoRNA-2 locus. The lengths of genes and intergenic regions are indicated; the shadow box designates the region present in the silencing construct; the dot-filled boxes mark the novel RNAs. FIG. 5b illustrates the putative secondary structures of the h2 and h3 RNAs. The secondary structures were obtained using the MFOLD program in Hypertext Transfer Protocol ://bioinfo (dot) math (dot) rpi.edu/~zukerm/rna/ and were modified to fit the canonical structure. The sequences are numbered and the AGA motif is boxed. FIGS. 5c-d illustrate the expression pattern of the h2 (FIG. 5c) and h3 (FIG. 5d) RNAs. Total RNA from L. collosoma (30 μg) was subjected to Northern blot analysis using the 22076 (SEQ ID NO:7) and h3-3A (SEQ ID NO:9) oligonucleotides which are complementary to the 3' end of h2 and h3, respectively. M=size marker (pBR322 DNA digested with MspI).

FIG. 6a is a schematic presentation of the snoRNA-2 locus. The shadow box indicates the silenced region; the oligonucleotides used in the RT-PCR reaction are indicated; the predicted size of PCR products is marked. FIG. 6b is an RT-PCR analysis depicting the level of snoRNA precursors in wild-type and snoRNA-2 silenced cells. RT-PCR was performed on RNA from wild-type cells or from snoRNA-2 silenced cells using the following primer pairs: lanes 1-4 with the g2 snoRNA precursor primers [26556 (SEQ ID NO:23) and 22078 (SEQ ID NO:24)] and lanes 5-6 with the snoRNA-2 precursor primers [22182 (SEQ ID NO:3) and h3-3A (SEQ ID NO:9)]. Lane 1—wild-type cells; lane 2—silenced cells; lanes 3 and 4-RT-PCR reactions as in lanes 1 and 2, however, devoid of RNA samples; lane 5—wild-type cells; lane 6—silenced cells. RT-PCR products were analyzed on a 2% agarose gel. Note that in both wild-type and silenced cells the g2 precursor transcript (marked with an open arrow) or the snoRNA-2 precursor transcript (marked with a closed arrow) are equally detected. M=1-kilobase DNA ladder. FIG. 6c is a primer extension analysis depicting silencing of the h2 RNA. Primer extension analysis was performed on wild-type (WT) or silenced (58-2) cells using the 22076 (SEQ ID NO:7) and 43388 (SEQ ID NO:8) oligonucleotides which are complementary to h2 and B5 snoRNAs, respectively. Note the similar intensity bands of the B5 transcripts in both cell lines (FIG. 6c, B5) and the decrease in band intensity in the silenced cells as compared with that of the wild-type cells (FIG. 6c, h2). FIG. 6d is a primer extension analysis depicting the level of h3 RNA. Primer extension analysis was performed on the same RNA as in FIG. 6b using the 20406 (SEQ ID NO:10), h3-3A (SEQ ID NO:9) antisense primers which are specific for B2 snoRNA and h3 RNA, respectively. Note the similar intensity bands of the B2 or h3 transcripts in both cell lines (FIG. 6d, B2, h3). M=size marker (pBR322 DNA digested with MspI).

FIG. 8a is a schematic presentation of the snoRNA antisense construct. The orientation of the neo-resistant gene and the snoRNA cluster are marked with arrows; The length of the insert is indicated. FIG. 8b illustrates primer extension analysis on RNA from wild-type cells (WT) and from cell lines carrying the construct expressing antisense transcript of the snoRNA cluster (i.e., silenced cells). The concentration of G418 used for selection is indicated above the lanes; The extension products are indicated and marked with arrows. Note the significant decrease in the level of sno270 in the silenced cells as compared with wild-type cells.

FIG. 9a is a schematic presentation of the opposing T7 construct. The orientation of the T7 promoters are indicated and marked with arrows. The genes in the cluster are given. FIGS. 9b-c illustrate primers extension analysis on TBC4 (FIG. 9b) and TBH1 (FIG. 9c). RNA from induced (2 days after tetracycline induction, Tet+) or uninduced (Tet−) cells was subjected to primer extension analysis using the TBC-4 (SEQ ID NO:15), TB H1 (SEQ ID NO:16) and 92a (SEQ ID NO:17) oligonucleotides complementary to the TBC4, TBH1 and snoRNA 92 (present in another locus) transcripts, respectively. Note the significant decrease (85%) in the level of the TBC4 in induced cells as compared with uninduced cells.

FIGS. 10a-b illustrate silencing of U14 snoRNA in human E14 cells. FIG. 10a is a schematic illustration depicting the construct used to silence the human U14 gene. The sequence in red designates the U14 sequence used to generate the U14 silencing construct [nucleotides 19-43 of the human U14 gene (GeneBank Accession No. NR_000022)] that was cloned into the pSUPER vector. The silencing construct insert with the h1 promoter that transcribes this gene was then cut from the pSUPER vector and subcloned into the pRETRO vector. FIG. 10b is a primer extension analysis demonstrating U14 silencing in cell lines transfected with the U14 silencing construct. RNA extracted from parental (lanes 1,3,5) or from U14 silenced cells (lanes 2, 4, 6) was subjected to primer extension analysis using the U14 primer (SEQ ID NO:44, lanes 1 and 2), U1 primer (SEQ ID NO:45, lanes 3 and 4) or the U14 and U1 primers together (lanes 5 and 6). Note the 50% reduction in the expression level of U14 in U14-silenced cells (lanes 2 and 6) as opposed to parental cells (lanes 1 and 5).

DESCRIPTION OF THE PREFERRED EMBODIMENTS

Figure 1A:
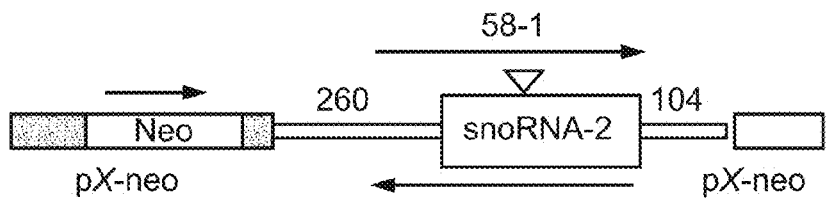
FIGS. 1a-b illustrate the expression of tagged snoRNA.

The present invention is of a method of downregulating small nuclear RNA which can be used to treat diseases associated with activity of small nuclear RNA. Specifically, the present invention can be used to downregulate snoRNA molecules or box H/ACA-containing RNA molecules which are involved in diseases such as cancer.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Small nuclear RNA molecules are important regulators of gene expression. For example, they participate in mRNA splicing [e.g., the U1, U2, U4 and U6 small nucleoplasmic RNAs (snRNAs)], mRNA and rRNA processing [e.g., the U7 snRNA, U3 and U8 small nucleolar RNAs (snoRNAs)] and site selection for RNA methylation (box C/D-snoRNA) or pseudouridine formation (box H/ACA-snoRNA). Another important nuclear RNA is the telomerase RNA (TER) which serves as a template for telomere replication, and in addition, contains a box H/ACA-like domain which confers functional localization of this RNA to the nucleus.

Abnormal expression of small nuclear RNA was shown to be involved in several diseases. For example, the majority of cancerous tumors contain active telomerase which contributes to cell transformation. In addition, trypanosome infections involve the expression of the parasite's snoRNA in the host cell.

Small nuclear RNA molecules are generally protected from targeted downregulation since they are present in the nucleus and thus are not exposed to molecules such as antisense oligonucleotides and RNAi which are typically active in the cytoplasm (Zeng, Y. and Cullen, B. R. 2002. RNA interference in human cells is restricted to the cytoplasm. RNA, 8: 855-860).

Several prior art studies describe various attempts to downregulate the telomerase RNA transcript. These studies which used thio-phosphoramidate antisense oligonucleotides [Akiyama, M, et al., 2003. Effects of oligonucleotide N3'Æ EP5' thio-phosphoramidate (GRN163) targeting telomerase RNA in human multiple myeloma cells. Cancer Res. 63: 6187-6194] or plasmids carrying the hTER gene in the sense and anti-sense orientation (Kosciolek, B A, et al., 2003 Inhibition of telomerase activity in human cancer cells by RNA interference. Mol. Cancer Ther. 2: 209-216) resulted in only moderate inhibition of telomerase activity. Moreover, since the vectors utilized in these studies contained relatively long dsRNA molecules, the observed effects can be related to inhibition of protein synthesis via the activation of protein kinase R (PKR) and the inactivation of eIF2a.

In sharp contrast to prior art attempts, the present inventor has shown for the first time effective siRNA mediated inhibition of a snoRNA.

Thus, according to one aspect of the present invention there is provided a method of downregulating a level of small nuclear RNA in a cell.

As used herein, the phrase "small nuclear RNA" refers to small RNA molecules which are synthesized and/or function in the nucleoplasm and/or the nucleolus of the cell. According to preferred embodiments the small nuclear RNA molecules of the present invention are small nucleolar RNAs (snoRNAs) which contain the box C/D or box H/ACA domains and the small nuclear RNA molecules which contain a box H/ACA-like domain.

Non-limiting examples of box C/D snoRNAs include the *L. collosoma* B2 (GenBank Accession No. AF331656), *L. collosoma* B3 (GenBank Accession No. AY046598), *L. collosoma* B4 (GenBank Accession No. AY046598), *L. collosoma* B5 (GenBank Accession No. AY046598), *L. collosoma* TS1 (GenBank Accession No. AF331656), *L. collosoma* TS2 (GenBank Accession No. AF331656), *L. collosoma* g2 (GenBank Accession No. AF331656), *L. collosoma* snoRNA-2 (GenBank Accession No. AF050095), *T. brucei* snoRNA 92 (GenBank Accession No. Z50171), *L. tarentolae* snoRNA 92 (GenBank Accession No. AF016399), *T. brucei* TBC4 snoRNA (SEQ ID NO:35), *T. brucei* sno 270 (GenBank Accession No. Z50171) and human U14 snoRNA (GenBank Accession No. NR_000022).

Non-limiting examples of box H/ACA snoRNA include the *L. collosoma* h1 (GenBank Accession No. AY046598), TBH1 (*T. brucei* Genome database No. ChrIX_pseudol.embl, 1386705-1386781), TBH2 (*T. brucei* Genome database No. ChrIX_pseudol.embl, 1386526-1386597), *T. brucei* SLA1 (GenBank Accession No. Z50171), *L. tarentolae* SLA1 (GenBank Accession No. AF016399), *L. collosoma* h2 (SEQ ID NO:28) and *L. collosoma* h3 (SEQ ID NO:30).

Non-limiting examples of small nuclear RNA molecules which contain a box H/ACA-like domain include the mouse telomerase RNA (TER) (GenBank Accession No. AY058900, SEQ ID NO:40) and the human TER (GenBank Accession No. NR_001566, SEQ ID NO:41).

According to this aspect of the present invention the method is effected by providing to the cell an isolated polynucleotide having a nucleic acid sequence selected suitable for inducing RNAi-mediated degradation of the small nuclear RNA thereby downregulating the level of the small nuclear RNA in the cell.

To enable RNAi-mediated degradation of small nuclear RNA, the isolated polynucleotide of the present invention includes a nucleic acid sequence which is at least 75%, at least 80%, at least 85%, at least 90%, at least 95%, more preferably, 98% or more identical to the polynucleotide sequence set forth by SEQ ID NO:14, 18, 29, 31, 34, 37, 38, 42 or SEQ ID NO:25, 28, 30, 32, 33, 36, 40, or 41 as determined using the BlastN software of the National Center of Biotechnology Information (NCBI) using default parameters.

As used herein, the term "RNAi" refers to the process of sequence-specific, post-transcriptional gene silencing in animals and plants, initiated by double-stranded RNA (dsRNA) that is identical to a region of a target RNA and leads to its degradation. Methods relating to the use of RNAi to silence genes in *C. elegans, Drosophila*, plants, and mammals are known in the art (Fire A, et al., 1998. Nature 391: 806-811; Fire, A. 1999. Trends Genet. 15: 358-363; Sharp, P. A. 2001. RNA interference. Genes Dev. 15: 485-490; Hammond, S.

M., et al., 2001. Nature Rev. Genet. 2: 110-1119; Tuschl, T. 2001. Chem. Biochem. 2: 239-245; Hamilton, A. et al., 1999. Science 286: 950-952; Hammond, S. M., et al., 2000. Nature 404: 293-296; Zamore, P. D., et al., 2000. Cell 101: 25-33; Bernstein, E., et al., 2001. Nature 409: 363-366; Elbashir, S. M., et al., 2001. Genes Dev. 15: 188-200; WO0129058; WO9932619, and Elbashir S M, et al., 2001. Nature 411: 494-498).

RNAi is a two-step process. In the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Cum Opin. Genetics and Development 12: 225-232 (2002); and Bernstein Nature 409: 363-366 (2001)].

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12: 225-232 (2002); Hammond et al. (2001) Nat. Rev. Gen. 2: 110-119 (2001); and Sharp Genes. Dev. 15: 485-90 (2001)]. Although the mechanism of cleavage is still to be elucidated, research indicates that each RISC contains a single siRNA and an RNase [Hutvagner and Zamore Curr. Opin. Genetics and Development 12: 225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2: 110-119 (2001), Sharp Genes. Dev. 15: 485-90 (2001); Hutvagner and Zamore Curr. Opin. Genetics and Development 12: 225-232 (2002)]. For more information on RNAi see the following reviews Tuschl Chem Biochem. 2: 239-245 (2001); Cullen Nat. Immunol. 3: 597-599 (2002); and Brantl Biochem. Biophys. Act. 1575: 15-25 (2002).

Figure 3A:
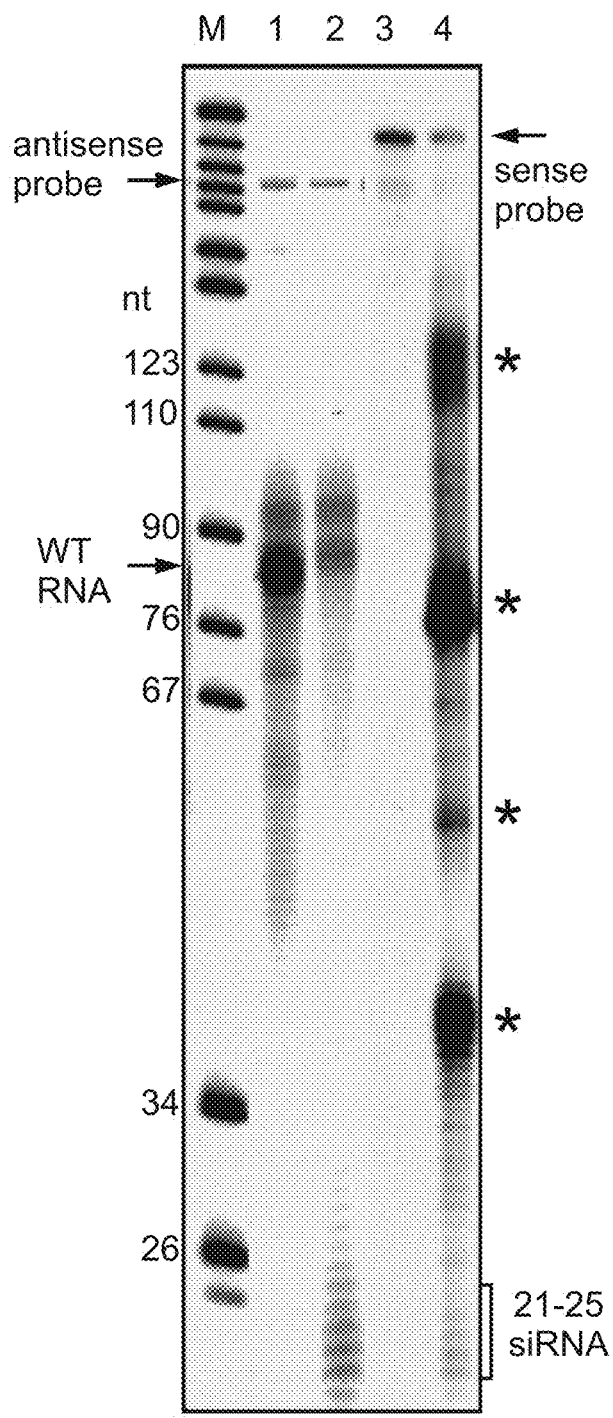
FIGS. 3a-c illustrate the detection of siRNAs.
Figure 3B:
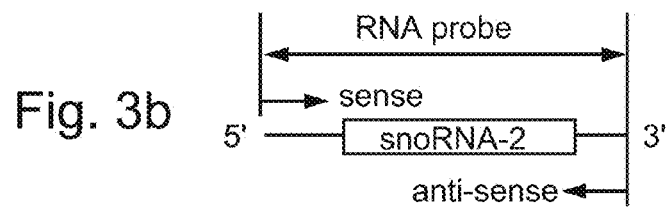
Figure 3C:
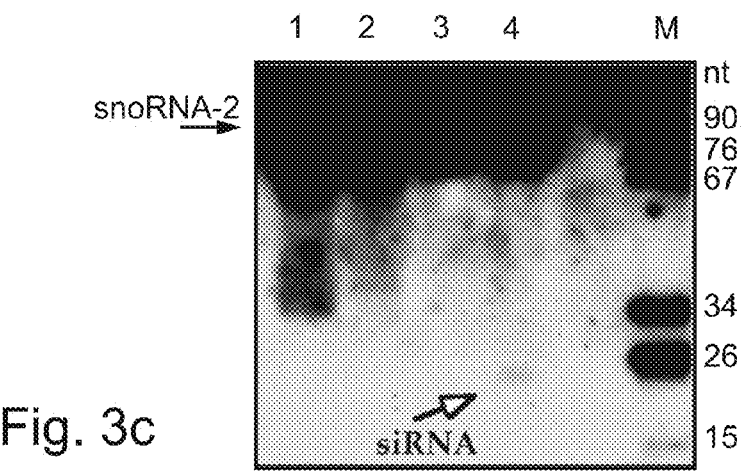

As is shown in FIG. 3c, the inhibition of snoRNA-2 in *L. collosoma* cells which were transfected with the antisense snoRNA-2 vector was mediated via the formation of low-molecular weight RNA molecules of 20-25 nucleotide in length, corresponding to siRNA molecules involved in RNAi.

Thus, in order to induce RNAi-mediated degradation of the small nuclear RNA, the isolated polynucleotide of the present invention is preferably a double-stranded RNA molecule which includes a sequence identical to a portion of the target small nuclear RNA.

According to preferred embodiments the sequence of the polynucleotide of the present invention is at least 15 and no more than 30 nucleic acids in length, more preferably, at least 18 and no more than 27, more preferably, at least 20 and no more than 25, most preferably, at least 22 and no more than 25 nucleic acids.

Figure 8A:
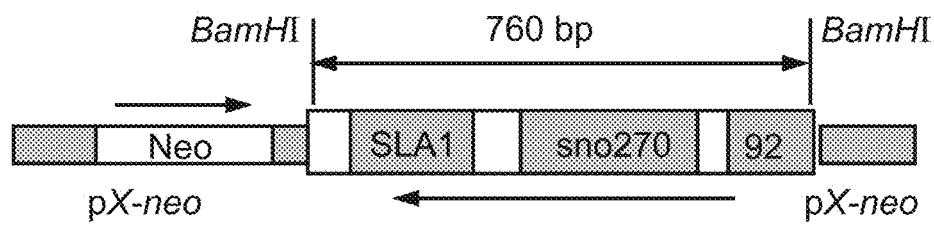
FIGS. 8a-b illustrate silencing of snoRNA in L. major by antisense RNA.
Figure 8B:
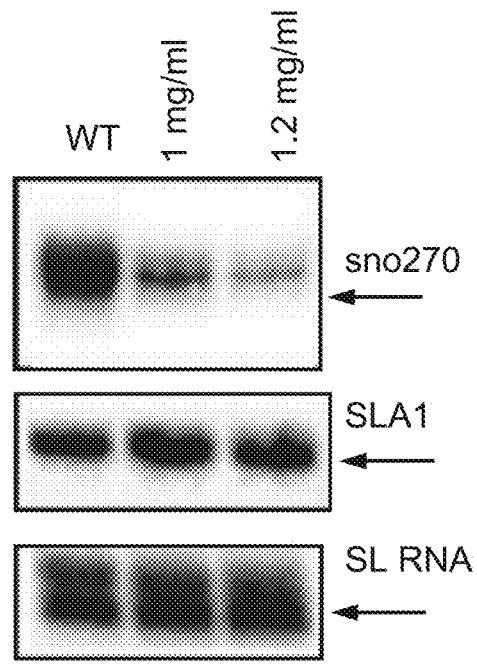

As is further shown in FIG. 8b and Example 5 of the Examples section which follows, a snoRNA siRNA polynucleotide which was expressed from a pZJM vector which includes the TBC4, TBC5 and TBH1 snoRNA cluster flanked by two opposing T7 promoters resulted in silencing of the snoRNA 270 gene in the *L. major* trypanosome.

Several approaches can be used to produce the polynucleotide of the present invention into a cell.

According to one preferred embodiments of the present invention the polynucleotide of the present invention can be produced by introducing into the cell a nucleic acid construct capable of expressing the polynucleotide described above.

In order to express the polynucleotide of the present invention in the cell a nucleic acid sequence is ligated into a nucleic acid construct which includes two promoters flanking the nucleic acid sequence. Such promoters are suitable for directing the transcription of the nucleic acid sequence in eukaryotic cells in a constitutive or inducible manner to thereby generate the polynucleotide of the present invention.

Constitutive promoters suitable for use with the present invention are promoter sequences which are active under most environmental conditions and most types of cells such as the CMV promoter, SV40 promoter, adenovirus major late promoter and Rous sarcoma virus (RSV). Inducible promoters suitable for use with the present invention include for example the hypoxia-inducible factor 1 (HIF-1) promoter (Rapisarda, A. et al., 2002. Cancer Res. 62: 4316-24) and the tetracycline-inducible promoter (Srour, M. A., et al., 2003. Thromb. Haemost. 90: 398-405).

The nucleic acid construct of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or RSV and HIV. See, Enhancers and Eukaryotic Expression, Cold Spring Harbor Press, Cold Spring Harbor, N.Y. 1983, which is incorporated herein by reference.

In the construction of the nucleic acid construct, the promoter(s) is preferably positioned at approximately the same distance from the heterologous transcription start site as it is from the transcription start site in its natural setting. As is known in the art, however, some variation in this distance can be accommodated without loss of promoter function.

In addition to the elements already described, the nucleic acid construct of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The nucleic acid construct may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The nucleic acid construct of the present invention can be used to express the polynucleotide of the present invention in mammalian cells (e.g., HeLa cells, Cos cells), yeast cells (e.g., AH109, HHY10, KDY80), insect cells (e.g., Sf9), trypanosome cells (e.g., *L. collosoma, L. major, T. brucei* 29-13) or bacteria cells (e.g., JM109, RP437, MM509, SW10).

Preferably, the polynucleotide of the present invention is synthesized by ligating a nucleic acid sequence (e.g., the nucleic acid sequence set forth by SEQ ID NO:18) into a mammalian, yeast, trypanosome or bacterial expression vector. Examples of such vectors include but are not limited to the pcDNA3.1, pBK-CMV and pCI vectors which are suitable for use in mammalian cells, the pGBKT7, pLGADH2-lacZ and pBGM18 vectors which are suitable for use in yeast cells, the pX-neo episomal vector which is suitable for use in trypanosome cells and the pACK02scKan, pMLBAD, pMLS7 vectors which are suitable for use in bacterial cells.

According to preferred embodiments the nucleic acid construct of the present invention is preferably constructed for eukaryotic expression, most preferably, mammalian cell expression.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Stratagene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Alternatively, the polynucleotide of the present invention is transcribed from nucleic acid constructs which can facilitate stable expression of the siRNA transcripts once introduced into a host cell. These constructs are engineered to express small hairpin RNAs (shRNAs), which are processed in vivo into siRNA molecules capable of carrying out gene-specific silencing [Brummelkamp, T. R., et al., (2002) A system for stable expression of short interfering RNAs in mammalian cells. Science 296: 550-53; Paddison, P. J., et al. (2002) Short hairpin RNAs (shRNAs) induce sequence-specific silencing in mammalian cells. Genes Dev. 16:948-58; Paul et al. (2002) Nature Biotech. 20: 505-08; Yu, J. Y., et al. (2002) RNA interference by expression of short-interfering RNAs and hairpin RNAs in mammalian cells. Proc. Natl. Acad. Sci. USA 99: 6047-52].

An example of a suitable nucleic acid construct is the pSUPER™, which includes the polymerase-III H1-RNA gene promoter with a well defined start of transcription and a termination signal consisting of five thymidines in a row (T5) [Brummelkamp, T. R. et al. (2002), Science 296: 550-53]. Most importantly, the cleavage of the transcript at the termination site is at a site following the second uridine, thus yielding a transcript which resembles the ends of synthetic siRNAs, which also contain nucleotide overhangs. siRNA is cloned such that it includes the sequence of interest, i.e., snoRNA sequence separated by a short spacer from the reverse complement of the same sequence. The resulting transcript folds back on itself to form a stem-loop structure, which mediates snoRNA RNAi.

Another suitable siRNA expression vector encodes the sense and antisense siRNA under the regulation of separate polIII promoters [Miyagishi and Taira (2002) Nature Biotech. 20: 497-500]. The siRNA, generated by this vector also includes a five thymidine (T5) termination signal.

Various methods can be used to introduce the nucleic acid construct of the present invention into mammalian cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation, microinjection, liposomes, iontophoresis, receptor-mediated endocytosis and infection with recombinant viral vectors. In addition, see U.S. Pat. Nos. 5,464,764 and 5,487,992 for positive-negative selection methods. For example, for stable transfection in dihydrofolate reductase deficient Chinese Hamster Ovary (CHO dhfr-) cells the expression vector of the present invention further includes a dihydrofolate reductase expression cassette positioned under a control of a thymidine kinase promoter.

Preferably, the nucleic acid construct of the present invention is delivered into the cell using retroviruses. Delivery of nucleic acid constructs using retroviruses provides several advantages over methods, such as lipofection, since retroviral delivery is more efficient, uniform and immediately selects for stable "knock-down" cells [Devroe, E. and Silver, P. A. (2002). Retrovirus-delivered siRNA. BMC Biotechnol. 2: 15].

It will be appreciated that the polynucleotide of the present invention can be chemically synthesized using for example, solid phase synthesis, as two complementary RNA oligonucleotides.

Several considerations must be taken into account when designing the synthetic polynucleotide of the present invention. For efficient in vivo inhibition of gene expression the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity. The binding affinity of double-stranded RNA oligonucleotides can be predicted (Walton et al., 1999, Biotechnol Bioeng 65: 1-9; Matveeva et al., 1998, Nature Biotechnology 16, 1374-1375; Zacharias M., Biopolymers. 2000, 54: 547-60).

Unmodified polynucleotides are typically impractical for use as RNAi sequences since they have short in vivo half-lives, during which they are degraded rapidly by nucleases.

Furthermore, they are difficult to prepare in more than milligram quantities. In addition, such polynucleotides are poor cell membrane penetrants.

Thus, in order to meet all the above listed requirements, the polynucleotide analogs need to be devised in a suitable manner.

For example, in order to improve half-life as well as membrane penetration, the polynucleotide backbone of the polynucleotide of the present invention can be modified.

Polynucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, anomeric bridges and borane derivatives (Cook, 1991, Medicinal chemistry of antisense oligonucleotides-future opportunities. Anti-Cancer Drug Design 6: 585). Preferably, to render an in vivo stability to the synthetic polynucleotide of the present invention, the oxygen molecule at position 2 of the ribose ring is methylated, resulting in 2'-O-methylated RNA oligonucleotides.

International patent application WO 89/12060 discloses various building blocks for synthesizing polynucleotide analogs, as well as polynucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form polynucleotide analogs. The linking moiety in the oligonucleotide analogs is selected from the group consisting of sulfide (—S—), sulfoxide (—SO—), and sulfone (—SO2-).

International patent application WO 92/20702 describe an acyclic oligonucleotide which includes a peptide backbone on which any selected chemical nucleobases or analogs are stringed and serve as coding characters as they do in natural RNA. These new compounds, known as peptide nucleic acids (PNAs), are not only more stable in cells than their natural counterparts, but also bind the natural RNA 50 to 100 times more tightly than the natural nucleic acids cling to each other. PNA oligomers can be synthesized from the four protected monomers containing uridine, cytosine, adenine and guanine by Merrifield solid-phase peptide synthesis. In order to increase solubility in water and to prevent aggregation, a lysine amide group is placed at the C-terminal region.

The synthetic polynucleotide of the present invention can be administered to the cells using various methods such as lipofection, electroporation and the like.

Recent scientific publications have validated the efficacy of siRNA molecules in inhibiting target mRNA expression and thus have clearly demonstrated the therapeutic potential of such molecules. For example, RNAi has been utilized to inhibit expression of hepatitis C (McCaffrey, A. P., et al., 2002, Gene expression: RNA interference in adult mice. Nature 418, 38-39), HIV-1 (Jacque, J-M., et al. 2002, Modulation of HIV-1 replication by RNA interference. Nature 418, 435-438), cervical cancer cells (Jiang, M., and Milner, J. 2002, Selective silencing of viral gene expression in HPV-positive human cervical carcinoma cells treated with siRNA, a primer of RNA interference. Oncogene 21, 6041-8) and leukemic cells [Wilda, M., et al., 2002, Killing of leukemic cells with a BCR/ABL fusion gene by RNA interference (RNAi). Oncogene 21, 5716-24].

Several prior art studies have shown that overexpression and/or abnormal activity of small nuclear RNA molecules can result in abnormal processing and/or activity of other biomolecules (e.g., rRNA, mRNAs).

For example, the brain-specific HBII-52 and HBII-85 C/D box snoRNAs were found to be related to imprinting as they were silenced in Prader-Willi syndrome (PWS) patients (Cavaillé, J. et al., 2000. Identification of brain-specific and imprinted small nucleolar RNA genes exhibiting an unusual genomic organization. Proc. Natl. Acad. Sci. USA. 97: 14311-14316).

In addition, it was found that overexpression of the human telomerase is involved in the progression of cancerous tumors. Moreover, processing of rRNA of parasites such as trypanosomes is also guided by parasite specific snoRNA (see Example 4 of the Examples section which follows).

Thus, the polynucleotide of the present invention can be utilized to treat diseases which are associated with abnormal activity or expression of small nuclear RNA molecules or activity of infection specific snoRNAs.

Figure 10B:
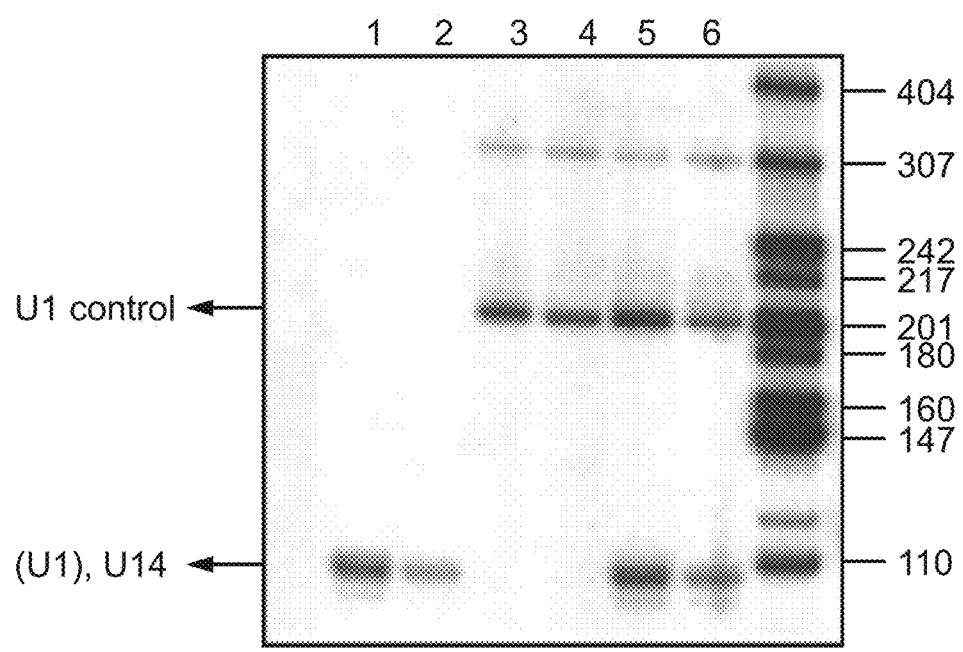

As is shown in FIG. 10b and in Example 6 of the Examples section which follows, a 50% reduction in the level of U14 snoRNA was shown in human E14 cells using a U14 snoRNA silencing construct including a U14 antisense sequence (SEQ ID NO:43). Moreover, as is further shown in Example 6 of the Examples section which follows, inhibition of U14 snoRNA in these human cells resulted in a 25% reduction in the methylation guided by this RNA on C462 of the 18S rRNA.

Thus, according to another aspect of the present invention, there is provided a method of treating a disease characterized by abnormal expression or activity of a biomolecule, wherein the biomolecule includes, associates with, synthesized via or modified by a small nuclear RNA.

The method according to this aspect of the present invention is effected by providing to cells of an individual having the disease a polynucleotide having a nucleic acid sequence selected suitable for inducing RNAi-mediated degradation of the small nuclear RNA, thereby downregulating the level of the small nuclear RNA in the cells and treating the disease.

As used herein the term "biomolecule" refers to an RNA or a protein molecule, the synthesis, processing, activity or assembly of which involves small nuclear RNAs.

As used herein the phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

The method according to this aspect of the present invention is effected by providing to cells of the individual the isolated polynucleotide of the present invention to thereby downregulate the level of the small nuclear RNA in the cells of the individual.

For example, in order to inhibit telomerase activity in cancerous cells, a polynucleotide sequence capable of inducing RNAi mediated degradation of the human telomerase RNA (GenBank Accession No. NR_001566, SEQ ID NO:41) can be provided to the individual having cancer to thereby suppress of treat the cancer. Such a polynucleotide can be for example 5'-GUCUAACCCUAACUGAGAAGG-3' (SEQ ID NO:46).

Providing can be effected by directly administering the polynucleotide of the present invention into the cells or by expressing the polynucleotide in cells as described hereinabove. Expressing can be effected by directly transfecting cells of the individual with a nucleic acid construct capable of expressing the polynucleotide of the present invention (i.e., in vivo transfection), or by transfecting cells isolated from the individual with the nucleic acid construct and administering the transfected cells to the individual (i.e., ex vivo transfection).

According to a preferred embodiment of the present invention, in vivo transfection is effected by administering the nucleic acid construct including the polynucleotide of the present invention into host tissues using a viral carrier.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I).

Recombinant viral vectors are useful for in vivo expression of the isolated polynucleotide of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

When retroviruses, for example, are used for polynucleotide transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

Mammalian cell systems which utilize recombinant viruses or viral elements to direct expression can be engineered. For example, when using adenovirus expression vectors, the polynucleotide of the present invention can be ligated to an adenovirus transcription/translation control complex, e.g., the late promoter and tripartite leader sequence. Alternatively, the vaccinia virus 7.5K promoter can be used (Mackett et al., Proc. Natl. Acad. Sci., USA 79:7415-7419, 1982; Mackett et al, J. Virol. 49:857-864, 1984; Panicali et al., Proc. Natl. Acad. Sci., USA 79:4927-4931, 1982). Particularly useful are bovine papilloma virus vectors, which can replicate as extrachromosomal elements (Sarver et al., Mol. Cell. Biol. 1:486, 1981). Shortly after entry of this DNA into mouse cells, the plasmid replicates to about 100 to 200 copies per cell. Transcription of the inserted cDNA yielding a high level of expression may result without integration of the plasmid into the host cell chromosome. These vectors can be used for stable expression by including a selectable marker in the plasmid, such as, for example, the neo gene. Alternatively, the retroviral genome can be modified for use as a vector capable of introducing and directing the expression of the polynucleotide of the present invention in the host cells (Cone and Mulligan, Proc. Natl. Acad. Sci., USA 81:6349-6353, 1984). High level expression can also be achieved using inducible promoters, including, but not limited to, the hypoxia-inducible factor (HIF)-1alpha promoter.

Additional expression vectors containing regulatory elements from eukaryotic viruses such as retroviruses include the SV40 vectors (e.g., pSVT7 and pMT2), the bovine papilloma virus vectors (e.g., pBV-1MTHA) and vectors derived from Epstein Bar virus (e.g., pHEBO and p2O5). Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As is mentioned above, ex vivo transfection is effected by transfecting cells isolated from the individual.

As is used herein the term "cells" refers to bone marrow cells, stem cells of various cell lineages, lymph node cells, and the like which are obtained from the individual via for example fine needle aspiration or a biopsy. The cells of the present invention are isolated from the individual and are optionally cultured under suitable culturing conditions using methods known in the arts.

It will be appreciated that in order to treat the disease the transfected cells are administered to the individual having the disease.

Administration of the cells of the present invention can be effected using any suitable route such as intravenous, intra peritoneal, intra hepatic, intra spleenic, intra pancreatic, subcutaneous, transcutaneous, intramuscular, intracutaneous, and/or injection in smooth muscle, using e.g., a catheter.

The cells of the present invention can be derived from either autologous sources such as self bone marrow cells or from allogeneic sources such as bone marrow derived from non-autologous sources. Since non-autologous cells are likely to induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly (allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyocinnamylideneacetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002, 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002, 13: 783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

The nucleic acid construct including the polynucleotide of the present invention and/or the synthetic polynucleotide of the present invention can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the nucleic acid construct containing the polynucleotide of the present invention and/or the synthetic polynucleotide of the present invention which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intra brain, intravenous, inrtaperitoneal, intranasal, or intraocular injections.

Alternately, one may administer the pharmaceutical composition in a local rather than systemic manner, for example, via injection of the pharmaceutical composition directly Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (the nucleic acid construct including the polynucleotide of the present invention and/or the synthetic polynucleotide of the present invention) effective to prevent, alleviate or ameliorate symptoms of a disorder (e.g., tumor progression) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide the tissue level of the active ingredient which is sufficient to treat the disease (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising the nucleic acid construct of the present invention formulated in a compatible pharmaceutical carrier may also be prepared, placed in an appropriate container, and labeled for treatment of an indicated condition, as if further detailed above.

It will be appreciated that the method of the present invention can be used to downregulate the level of other important RNA molecules which function in the nucleus.

Examples include, but are not limited to the RNase P and RNase mitochondrial RNA processing (MRP) which are concentrated in the nucleoli and Cajal bodies (Cai, T., et al., 2002. The *Saccharomyces cerevisiae* RNase mitochondrial RNA processing is critical for cell cycle progression at the end of mitosis. Genetics 161: 1029-1042) and are involved in the processing of 5' leader sequence of tRNA and the cleavage at the A3 site in the internal transcribed spacer 1 of rRNA precursors, respectively. It was found that mutations in the RNase MRP RNA cause cartilage hair hypoplasia, which is manifested by abnormal body growth and development of predisposition to tumors of the lymphatic organs (Ridanpaa, M., et al., 2001. Mutations in the RNA component of RNase MRP cause a pleiotropic human disease, cartilage-hair hypoplasia. Cell 104: 195-203).

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat.

Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Construction of a snoRNA-2 plasmid vector—was performed essentially as described elsewhere (Xu Y et al., J. Biol. Chem. 2001, 276: 14289-98). Briefly, a fragment containing the snoRNA-2 gene (SEQ ID NO:18) including 260 and 104 bp flanking sequences from the 5' and 3' ends, respectively, was cloned into the BamHI site of the pX-neo (Kapler G M, Coburn C M, Beverley S M. 1990. Stable transfection of the human parasite Leishmania major delineates a 30-kilobase region sufficient for extrachromosomal replication and expression. Mol. Cell. Biol. 10: 1084-94) episomal vector which carries the neomycine (neo) resistance gene upstream of the cloning site.

Construction of an L. major silencing vector—The L. major locus encoding for snoRNA 92, 270 and SLA1 was PCR-amplified using the LmSLA-5B (SEQ ID NO:19) and LmSLA-3B (SEQ ID NO:20) primers and cloned into the BamHI site of the pX-neo expression vector in an opposite orientation with respect to the neo-resistant gene.

Construction of an T. brucei silencing vector—The T. brucei snoRNA cluster carrying the TBC4, TBC5 and TBH1 genes was amplified by PCR using the Sno-1-5XH (SEQ ID NO:21) and Sno-1-3H (SEQ ID NO:22) primers. The fragment was cloned into the XhoI and HindIII sites of the pZJM expression vector (Wang, Z., et al., 2000 Inhibition of Trypanosoma brucei gene expression by RNA interference using an integratable vector with opposing T7 promoters. J. Biol. Chem. 275: 40174-9) in between the two T7 opposing promoters as depicted in FIG. 8a. The construct was linearized with NotI before transfection.

Transfection and preparation of cell lines—L. collosoma (obtained from Dr. Nina Agabian, UCSF, CA, USA), T. brucei (24/13 strain) or L. major (MHOM/IL/80/Fredlin) cells were transfected with the silencing constructs essentially as described elsewhere (Xu, Y., et al., 2001, J. Biol. Chem. 276, 14289-14298) and clone selection was performed in the presence of G418.

Primer extension analysis—Primer extension analyses were performed essentially as described by Xu, Y et al., 2001 (J. Biol. Chem., 276: 14289-14298) using the oligonucleotides listed in Table 1, hereinbelow.

Mapping the 2'-O-methylated nucleotides—was performed using 5'-labeled 19796 anti-sense oligonucleotide (SEQ ID NO:6) complementary to the 5.8S rRNA in the presence of increasing concentration of dNTPs ranging from 0.05 to 5 mM.

TABLE 1

Oligonucleotides used for primer extension, RT-PCR or Northern Blot analyses

| Oligonucleotide name (SEQ ID Nos.) | Sequence from 5'→3' | Description |
|---|---|---|
| 16865 (SEQ ID NO: 1) | CATCAGATGCCGGTAGTC | anti-sense, complementary to L. collosoma snoRNA-2 gene, from position 67 to 83 |
| 43362 (SEQ ID NO: 2) | CAATCTTGCACAGTGTCG | anti-sense, complementary to L. collosoma h1 snoRNA, from positions 52 to 69 |
| 22182 (SEQ ID NO: 3) | ACGTTCTGCAATCTGACCGCG | sense, specific for L. collosoma snoRNA-2 gene, from 18 to 39 |
| 12407 (SEQ ID NO: 4) | AGCTATATCTCTCGAA | complementary to L. collosoma U6 RNA, from positions 83 to 98 |
| 36815 (SEQ ID NO: 5) | GAGGGAGGAATGAGGTGAGC | complementary to neo/hygro mRNA, from position 4996 to 5016 on the pX vector |
| 19796 (SEQ ID NO: 6) | CGCCGTTTGCGTTCA | anti-sense, complementary to L. collosoma 5.8S rRNA, from positions 101 to 115 |
| 22076 (SEQ ID NO: 7) | CG<u>GGATCC</u>TGCCAGAATTGTCCCGTGC | anti-sense, containing a BamHI site, complementary to L. collosoma h2 snoRNA, from positions 43 to 62 |
| 43388 (SEQ ID NO: 8) | ACAGCTACCGCGAGTTGC | anti-sense, complementary to L. collosoma B5 C/D snoRNA from position 59 to 76 |

TABLE 1-continued

Oligonucleotides used for primer extension, RT-PCR or Northern Blot analyses

| Oligonucleotide name (SEQ ID Nos.) | Sequence from 5'→3' | Description |
|---|---|---|
| h3-3A (SEQ ID NO: 9) | CACTCTTTGGGGCGTTTC | anti-sense complementary to *L. collosoma* h3 snoRNA, from 47 to 64 |
| 20406 (SEQ ID NO: 10) | TTTCACATGCACGAGCATCC | anti-sense, complementary to *L. collosoma* B2 snoRNA, from position 36 to 55 |
| 4139 (SEQ ID NO: 11) | TTGCCGGAAGACGGGTTCCGGA | antisense, complementary to the spliced leader associated RNA (SLA RNA) of *L. major*, from positions 52 to 73 |
| 31253 (SEQ ID NO: 12) | TCTYGCTCTCCAGTTTCRTG | antisense, complementary to SLA1 RNA of *L. major*, from positions 47 to 66, carrying three mismatches |
| Lm270A (SEQ ID NO: 13) | AGCAACTCGAGGCCGT | *L. major* snoRNA 270, from positions 55 to 70 |
| TBC-4 (SEQ ID NO: 15) | ATAGAGTTCACAGTTGCA | antisense, complementary to *T. brucei* TBC4 snoRNA, from positions 57 to 74. |
| TB-H1 (SEQ ID NO: 16) | AATTCTCGGACCACGTGA | antisense, complementary to *T. brucei* TBH1 snoRNA, from positions 60 to 77. |
| 92a (SEQ ID NO: 17) | CCGTCGCAGATGGACGTTGA | antisense, complementary to snoRNA 92 of *T. brucei*, from positions 31 to 50 |
| LmSLA-5B (SEQ ID NO: 19) | CGGGATCCGCTGCGCGTTGACATG | sense, carrying a BamHI site, specific to the 5' junction sequence of *L. major* snoRNA 92, from positions -12 to +6 |
| LmSLA-3B (SEQ ID NO: 20) | CGGGATCCAGCGGCGTCCCACGCAGC | antisense, carrying a BamHI site, specific to the downstream flanking sequence of *L. major* SLA1, from positions +179 to +198 |
| Sno-1-5XH (SEQ ID NO: 21) | CCGCTCGAGTTACCTATTCCATGCACATT | sense, carrying a XhoI site, specific to the upstream flanking sequence of *T. brucei* TBC-4 snoRNA, from positions -44 to -63 |
| Sno-1-3H (SEQ ID NO: 22) | CCCAAGCTTGAGAAGAGTGTGCACTAACC | antisense, carrying a HindIII site, complementary to downstream flanking sequence of *T. brucei* TBH1 snoRNA, from positions +16 to +35 |
| 26556 (SEQ ID NO: 23) | TGAGACCCGCCGACCCGAAT | sense, specific to upstream flanking sequence of *L. collosoma* G2 snoRNA, from positions -80 to -100 |
| 22078 (SEQ ID NO: 24) | CGGGATCCAAAGAGAGGGACGCGACA | antisense, complementary to downstream flanking sequence of *L. collosoma* G2 snoRNA, from positions +40 to +58, carrying a BamH I site |
| U14 antisense (SEQ ID NO: 43) | CCAGACATTCGCAGTTTCCACCAG | antisense, complementary to positions 19-43 of U14 |
| U14 primer extension primer (SEQ ID NO: 44) | TTC CAC CAG TCT CTT GAA | Primer extension oligonucleotide from Human U14 snoRNA |
| U1 primer extension primer (SEQ ID NO: 45) | AGC GCG AAC GCA GTC CCC | Primer extension oligonucleotide from Human U1 |

Table 1: Oligonucleotide sequences and positions along the following genes are provided. *L. collosoma* SnoRNA-2 gene (GenBank Accession No. AF050095, SEQ ID NO: 18); *L. collosoma* h1 snoRNA (GenBank Accession No. AY046598, SEQ ID NO: 25); U6 RNA (GenBank Accession No. X79014, SEQ ID NO: 26); *Leptomonas mirabilis* 5.8S rRNA (GenBank Accession No. AY180153, SEQ ID NO: 27); *L. collosoma* h2 snoRNA (SEQ ID NO: 28); B5 C/D snoRNA (GenBank Accession No. AY046598, SEQ ID NO: 29); h3 snoRNA (SEQ ID NO: 30); *L. collosoma* B2 snoRNA (GenBank Accession No. AF331656, SEQ ID NO: 31); spliced leader associated RNA (SLA1 RNA) of *L. tarentolae* (GenBank Accession No. AF016399, SEQ ID NO: 32); SLA1 of *T. brucei* (GenBank Accession No. Z50171, SEQ ID NO: 33); snoRNA 270 (GenBank Accession No. Z50171, SEQ ID NO: 14); *L. collosoma* g2 snoRNA (GenBank Accession No. AF331656, SEQ ID NO: 34); *T. brucei* TBC4 snoRNA (*T. brucei* Genome database No. ChrIX_pseudo1.embl, 1385500-1387000, SEQ ID NO: 35), *T. brucei* TBH1 snoRNA (*T. brucei* Genome database No. ChrIX_pseudo1.embl, 1386705-1386781, SEQ ID NO: 36), *T. brucei* snoRNA 92 (GenBank Accession No. Z50171, SEQ ID NO: 37); *L. tarentolae* snoRNA (GenBank Accession No. AF016399, SEQ ID NO: 38), neo/hygro mRNA on the pX vector (SEQ ID NO: 39), human U14 snoRNA (GenBank Accession No. NR_000022, SEQ ID NO: 42)., Underlined nucleotides in primer sequences represent restriction enzyme recognition sites.

Synthesis of RNA probes—RNA probes were transcribed from linearized pGEM plasmid DNA containing the wild-type snoRNA-2 gene essentially as described elsewhere (Michaeli, S., et al., 1990. J. Biol. Chem. 265, 10582-10588). Briefly, plasmid DNA containing the snoRNA-2 gene (pGEM T Easy Vector) was linearized using the SalI or EcoRI restriction enzymes (New England Biolabs, Beverly, USA) and the antisense or sense RNA probes were transcribed using the T7 or SP6 RNA polymerases (Promega Co., Madison, Wis., USA), respectively.

RNase protection—Total RNA (30 μg) was mixed with 100,000 cpm of gel-purified RNA probe and concentrated by ethanol precipitation. The pellet was dissolved in hybridization buffer [40 mM PIPES (pH 6.4), 80% formamide, 0.4 M sodium acetate, 1 mM EDTA], all provided from Sigma-Aldrich CO., Louis, Mo., USA. RNA-probe samples were boiled for 1 minute and hybridized for 14-16 hours at 45° C. Following hybridization, the samples were diluted 1:10 with a solution consisting of [10 mM Tris-HCl (pH 7.5), 5 mM EDTA, 200 mM Sodium acetate, all provided from Sigma-Aldrich CO., St Louis, Mo., USA] containing 2.5 unit/ml RNase ONE (Promega Corp., Madison, Wis., USA). RNase digestion was performed for 1 hour at 30° C. and terminated by Proteinase K digestion (Roche Diagnostics Co., Indianapolis, USA). Following phenol-chloroform extraction, the protected products were precipitated with ethanol in the presence of 20 μg glycogen and analyzed on an 8% polyacrylamide-7M urea denaturing gel essentially as described in Xu, Y et al., 2001 (J. Biol. Chem. 276: 14289-14298).

Northern blot hybridization—For detection of small interfering RNAs (siRNAs), 40-80 μg of total RNA samples were electrophoresed on 10% polyacrylamide-7M-urea denaturing gels and electroblotted at 25 mA for 5-7 hours to nylon membranes (Hybond, Amersham Biosciences, Inc, Piscataway, N.J., USA). The membranes were hybridized at 42° C. using the snoRNA-2 antisense RNA probe. Following hybridization, the blot was washed twice for 20 minutes at 45° C. with 300 mM NaCl, 30 mM NaCitrate (2×SSC) and 0.1% SDS.

Cellular fractionation—*L. collosoma* cells ($2 \times 10^9$) propagated at the log phase were pelleted and washed with phosphate-buffered saline (PBS). The pellet was resuspended in 35 mM HEPES (pH 7.9), 10 mM $MgCl_2$, 24 mM KCl, 50 μg/ml leupeptine (all provided from Sigma-Aldrich CO., St Louis, Mo., USA), 5 mM β-mercaptoethanol (Merck-Schuchardt, Munchen, Germany). Prior to cell homogenizing, NP-40 (Sigma-Aldrich) was added to a final concentration of 0.3%, and the cells were disrupted by 20 strokes of a dounce homogenizer. The cell lysate was centrifuged for 10 minutes at 10,000×g and the nuclear fraction (pellet) was separated from the cytoplasmic fraction (supernatant). RNA was prepared from the cytoplasmic fraction using standard phenol extraction and from the nuclear fraction using TRIzol reagent (Sigma-Aldrich Corp., St Louis, Mo., USA).

Example 1

The Level of snoRNA-2 Expression Varies with the Level of Anti-Sense snoRNA-2 Transcript The expression of the tagged *L. collosoma* snoRNA-2 gene from an episomal vector is dependent on the orientation of the gene with respect to the resistant gene on the episome. Thus, when the tagged snoRNA gene is expressed in a transcriptional direction of the neo gene, the expression of the tagged gene is efficient. On the other hand, since episomal vectors in Leishmania are transcribed from both strands (Laban, A., et al., 1990. *Nature* 343, 572-574), the lack of expression of the tagged gene when cloned in the opposite was attributed to the differential efficiency of transcription from the two strands of the episomal vector. In order to search for a putative snoRNA promoter that will enhance transcription of the snoRNA gene when present in the opposite orientation, cell lines carrying the snoRNA-2 in two orientations were generated, as follows.

Experimental Results

Figure 1B:
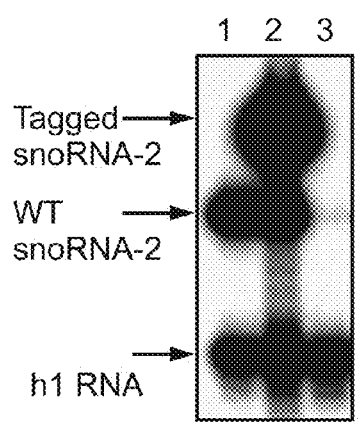

Expression of the antisense snoRNA-2 transcript downregulates both the tagged and wild-type snoRNA-2 genes— The snoRNA-2 gene was cloned in the same or the opposite direction of the neo gene of the pX-neo episomal vector (FIG. 1a) and cell lines transfected with the pX-neo vector were selected in the presence of 600 μg/ml of G418. RNA extracted from the transfected cells was subjected to primer extension analysis using the 16865 antisense oligonucleotide (SEQ ID NO:1) which recognizes both the tagged and wild-type snoRNA-2 transcripts. As is shown in FIG. 1b, when the snoRNA gene was in the same direction as the neo gene, the tagged gene was efficiently expressed (FIG. 1b, lane 2). However, when the snoRNA gene was placed in the opposite direction to the neo gene, no expression of the tagged (FIG. 1b, lane 3) or wild-type (FIG. 1b, lane 3) snoRNA-2 transcripts was detected. On the other hand, similar levels of expression were detected for the h1RNA transcript in either construct orientation (FIG. 1b, lanes 1-3). Thus, these results demonstrate that in snoRNA-2—transfected cells the expression level of the tagged or wild-type snoRNA-2 transcripts depends on the orientation of the snoRNA-2 gene relative to the orientation of the neo gene.

Figure 2A:
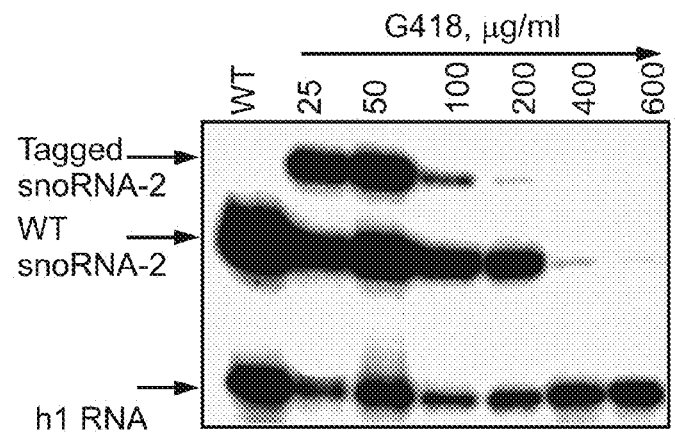
FIGS. 2a-c illustrate the effect of increased production of antisense snoRNA-2 on silencing of the snoRNA-2. Cell lines carrying the pX-neo episomal vector harboring the snoRNA-2 in the opposite orientation of the neo gene (i.e., antisense direction) were selected at increasing concentrations of G418. RNA extracted from the cell lines was subjected to primer extension analysis using the following oligonucleotides: h1-snoRNA—43362 (SEQ ID NO:2); snoRNA-2—16865 (SEQ ID NO:1); neo mRNA—36815 (SEQ ID NO:5); sense primer to the 5' end of snoRNA-2-22182 (SEQ ID NO:3).
Figure 2B:
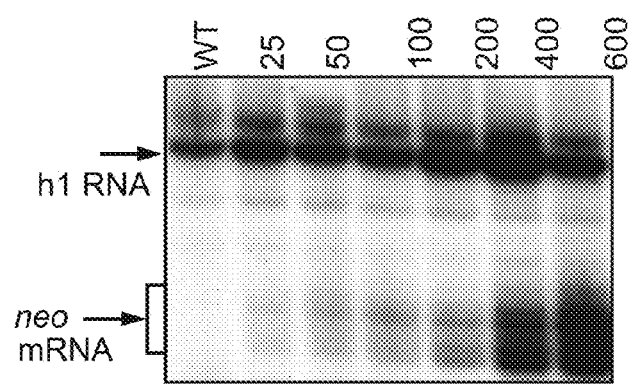
Figure 2C:
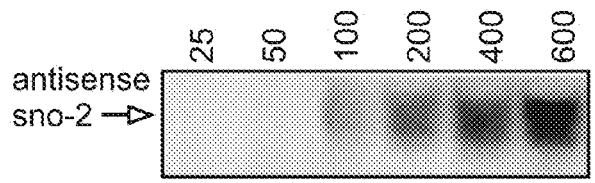

The expression of the snoRNA-2 gene is dependent on the level of the snoRNA-2 antisense transcript—To understand the mechanisms leading to snoRNA-2 silencing, transfected cells were selected using increasing concentrations of G418 and the levels of the tagged or wild-type snoRNA-2 transcripts (FIG. 2a), the neo transcript (FIG. 2b) or the antisense snoRNA-2 transcript (FIG. 2c) were determined. As is shown in FIG. 2a, at low concentrations of G418 (25-50 μg/ml), the tagged snoRNA-2 gene was efficiently expressed (FIG. 2a). However, when the concentration of G418 was increased to 100-200 μg/ml and beyond, the expression level of the tagged snoRNA-2 gene was significantly decreased (FIG. 2a). Similarly, the level of the wild-type snoRNA-2 gene, which was relatively high in the presence of 25-200 μg/ml G418, significantly decreased when the concentration of G418 was in the range of 400-600 μg/ml (FIG. 2a). On the other hand, increased concentrations of G418 resulted in increased levels of the neo transcript (FIG. 2b). Moreover, as is shown in FIG. 2c, high concentrations of G418 (100-600 μg/ml) resulted in increased levels of the snoRNA-2 antisense transcript which is transcribed in the neo direction.

Thus, these results demonstrate that under high concentrations of G418, the expressed antisense snoRNA-2 transcript elicits the degradation of both tagged and wild-type snoRNA-2 transcripts.

Example 2

Silencing of snoRNA-2 is Mediated Via the Production of siRNAs

It has been recently suggested that antisense effects may result from the production of small interfering RNA (siRNA) molecules (e.g., the *drosophila* in vitro RNAi silencing system, see Zamore, P. D. et al., 2000, 101: 25-33). To examine whether the snoRNA-2 silencing effect observed using the snoRNA-2 antisense construct (i.e., when the snoRNA-2 gene is in the opposite direction to the neo gene) was a result of RNAi, snoRNA-2 silenced cells were subjected to an RNase protection assay and Northern blot analysis, as follows.

Experimental Results

SiRNA is detected in cells carrying the snoRNA-2 antisense construct—To search for the presence of siRNA in cells transfected with the snoRNA-2 antisense construct, RNA was subjected to an RNase protection assay. As is shown in FIG. 3a, small RNA fragments (20-26 nucleotides) were detected using the sense and antisense snoRNA-2 probes in cells transfected with the snoRNA-2 antisense construct. The pattern of the protected small RNA fragments resembled the pattern of siRNA fragments reported by prior arts (Sijen, T., et al. 2001. Transcriptional and posttranscriptional gene silencing are mechanistically related. Curr Biol. 11: 436-40; Sijen, T., et al. 2001. On the role of RNA amplification in dsRNA-triggered gene silencing. Cell 107: 465-76). Thus, these results suggest the presence of siRNAs in cells transfected with the snoRNA-2 antisense construct.

To verify the presence of siRNA in the transfected cell lines, RNA extracted from wild-type cells or from cells transfected with the snoRNA-2 antisense construct was subjected to Northern blot analysis. As is shown in FIG. 3c, when transfected cells were selected in the presence of 600 μg/ml of G418, a clear hybridization band of approximately 25 nucleotides was detected.

Altogether, these results suggest the existence of siRNA in cells transfected with the snoRNA-2 antisense construct that were selected in the presence of high concentrations of G418. Taking together with the results presented in Example 1 hereinabove, these results suggest the involvement of the siRNA mechanism in the degradation of the snoRNA-2 transcript in cell transfected with the snoRNA-2 antisense construct.

Example 3

Cellular Distribution of siRNAs

The prior arts teach that snoRNAs are transcribed and processed in the nucleoplasm and then migrate to the nucleolus where they function (Kiss, T. 2002. Cell 109: 145-148). However, it is unclear where does the snoRNA's silencing process take place. To follow the silencing process of snoRNAs the cellular distribution of the snoRNA-2-specific siRNAs was determined, as follows.

Experimental Results

Figures 4A, 4B, 4C:
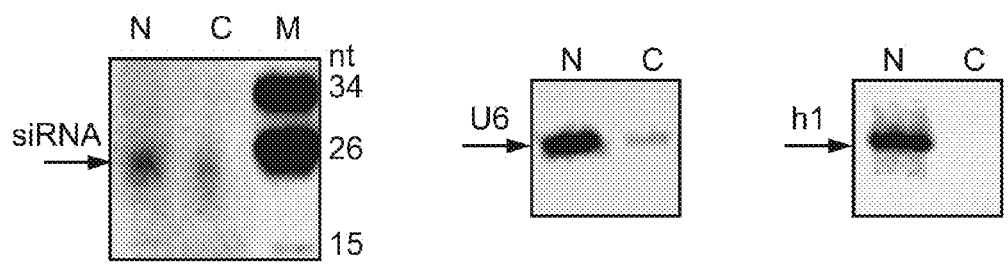
FIGS. 4a-d illustrate the cellular localization of snoRNA-2 siRNA, h1 snoRNA, U6 snRNA and 5.8S rRNA as detected using Northern blot analysis. RNA was prepared from the nuclear and cytoplasmic fractions of snoRNA-2 silenced cells that were selected in the presence of 600 μg/ml G418.
Figure 4D:
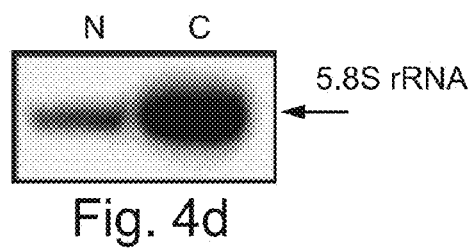

SiRNAs specific to snoRNA-2 are present in both the cellular and nuclear compartments—To determine the cellular localization of snoRNA-2-specific siRNAs, RNA was extracted from the nuclear or cytoplasmic compartments of cells transfected with the snoRNA-2 antisense construct and was further subjected to Northern blot analysis using snoRNA-2 antisense probe. As is shown in FIG. 4a, while a major hybridization band corresponding to the snoRNA-2-specific siRNA was detected in the nuclear fraction, a fainter, yet the same size band, was detected in the cytoplasmic fraction. To rule out the possibility of leakage from the nucleoplasm, the same RNA samples was hybridized using probes specific to the U6 snRNA (a nucleoplasm RNA), h1 snoRNA (a nucleolar RNA) or a 5.8S RNA (cytoplasmic RNA). As is shown in FIGS. 4b-d, while the h1 snoRNA was detected in the nuclear fraction alone (FIG. 4c), the U6 snRNA was detected mainly in the nuclear fraction with some leakage in the cytoplasmic fraction (FIG. 4b). On the other hand, the level of the 5.8SrRNA was, as expected, higher in the cytoplasmic fraction than in the nuclear fraction (FIG. 4d). Further analysis of the ratio between the level of the siRNA and U6 RNA in both compartments suggested that the level of the siRNA in the cytoplasmic compartment is higher than would have been expected solely from "leakage" from the nucleoplasm. Altogether, these results suggest that siRNAs may be produced both in the nucleus and the cytoplasm.

Example 4

Silencing of snoRNA-2 and H2 Does Not Take Place at the Precursor Level

The initial analysis of the snoRNA-2 cluster revealed only a single C/D snoRNA (Levitan, A., et al., 1998. Nucleic Acids Res. 26, 1775-1783). However, the recent discovery that snoRNA gene clusters in trypanosomes carry both H/ACA-like and C/D snoRNAs (Liang, X. H., Liu, L., Michaeli, S. 2001. J. Biol. Chem. 276: 40313-40318) has led the search for H/ACA-like RNAs in the snoRNA-2 cluster.

Experimental Results

Figure 5C:
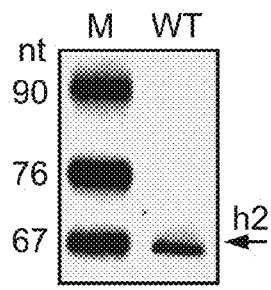
Figure 5D:
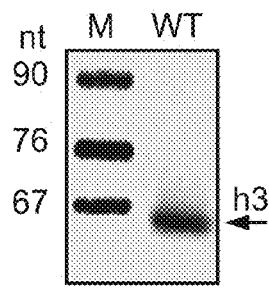

Characterization of the snoRNA-2, h2 and h3 cluster—The snoRNA-2 was found to be part of a gene cluster including two additional coding sequences of novel RNA which were termed h2 and h3 (Liang, X. H. et al., Small nucleolar RNA clusters in trypanosomatid *Leptomonas collosoma*, 2003, J. Biol. Chem. 279: In press). The gene organization within the snoRNA-2, h2 and h3 cluster is depicted in FIG. 5a and the secondary structure of the two novel RNAs is illustrated in FIG. 5b. In order to determine the expression pattern of the two novel genes, Northern blot analysis was performed on RNA samples extracted from the *L. collosoma* cells. Using the 22076 (SEQ ID NO:7) and h3-3A (SEQ ID NO:9) oligonucleotide probes which are specific to the h2 and h3 transcripts, respectively, it was found that both h2 and h3 genes are expressed in the wild-type *L. collosoma* cells (FIG. 5c).

The h2 and h3 RNAs exist in a polycistronic transcript with the snoRNA-2 transcript—In order to determine if the two novel RNA transcripts exist as a polycistronic transcript, RT-PCR analysis was performed using the 22182 (SEQ ID NO:3) and h3-3A primers (SEQ ID NO:9). As is shown in FIG. 6b, the presence of 330 nucleotide-long transcript suggests that the h2 and h3 transcript exist as a polycistronic RNA with the snoRNA-2 transcript.

Figure 6A:
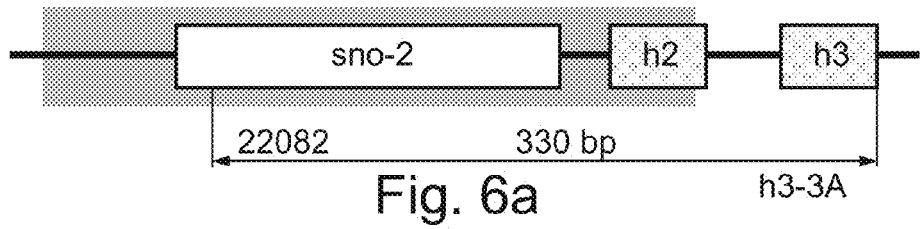
FIGS. 6a-d illustrate the presence of stable pre-snoRNA transcript in snoRNA-2 silenced cells.
Figure 6B:
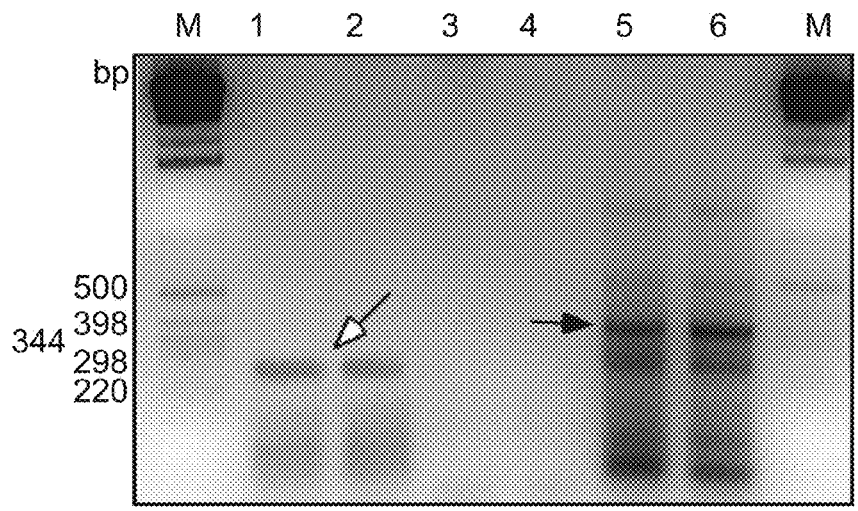

The polycistronic transcript is not degraded in snoRNA-2 silenced cells—As is further shown in FIG. 6b, equal levels of the snoRNA-2 polycistronic transcript were detected in both wild-type and silenced cells (FIG. 6b, lanes 5 and 6). These results suggest that snoRNA-2 silencing does not take place on the snoRNA-2 precursor transcript, but rather on the mature transcript. Similar results were obtained with the g2 precursor transcript (FIG. 6b, lanes 1 and 2) which was used as a control for these experiments.

Figure 6C:
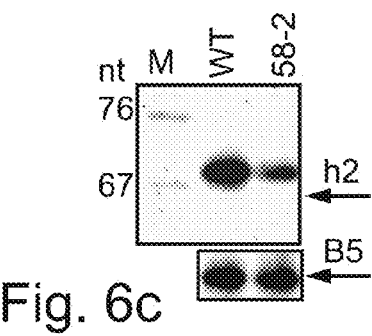
Figure 6D:
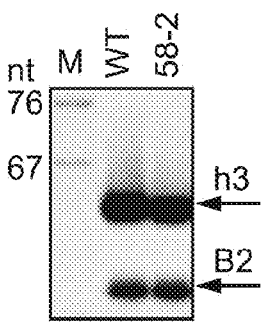

As is shown in FIG. 6a, the antisense snoRNA-2 construct carries in addition to the snoRNA-2 gene, part of h2 gene but not the h3 gene. To further substantiate the finding that silencing does not occur on the precursor transcript, the level of h2 and h3 transcripts was determined in wild-type or silenced cells using primer extension analyses. As is shown in FIGS. 6c-d, while the level of the h2 transcript was partially reduced in the silenced cells (FIG. 6c), the level of the h3 transcript remained unchanged (FIG. 6d). Altogether, these results demonstrate that in snoRNA-2 silenced cells the silencing process takes place at the mature and not the precursor polycistronic transcript.

Figure 7:
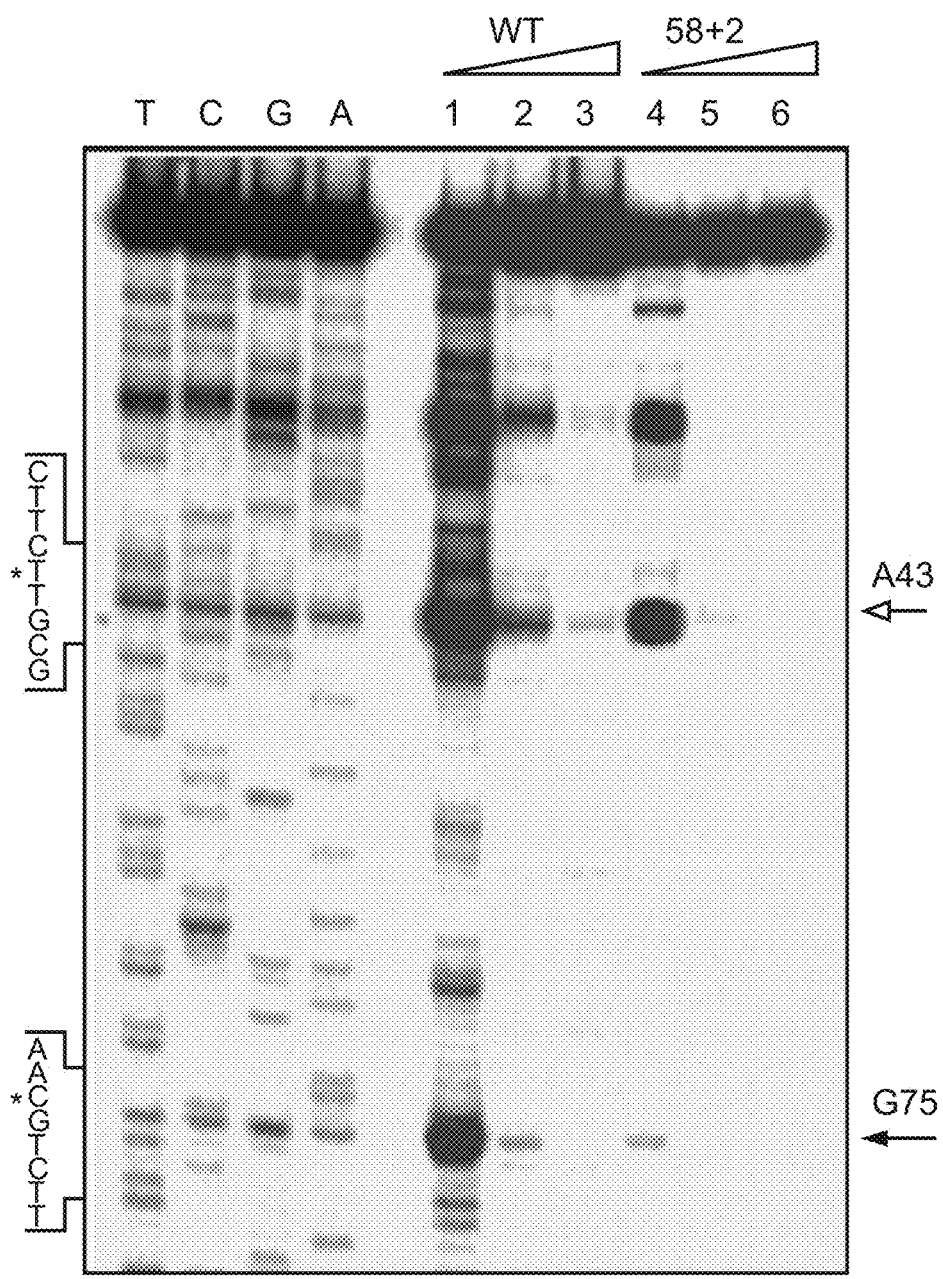
FIG. 7 is a primer extension analysis depicting the mapping of the ribose-methylated sites on 5.8S rRNA guided by snoRNA-2. Primer extension was performed on RNA from wild-type (WT, lanes 1-3) or snoRNA-2 silenced (58+2, lanes 4-6) cells in the presence of increasing concentrations of dNTPs (0.05, 0.5, and 5 mM) using the 19796 antisense oligonucleotide (SEQ ID NO:6), specific for 5.8S rRNA. The extension products were separated on an 8% polyacrylamide-7M urea denaturing gel next to primer extension sequencing performed using the same primer. Note that the reverse transcriptase stops at one nucleotide before the G75 (closed arrow) or A43 (open arrow) methylated sites. Partial sequence of the cDNA is presented and the methylated nucleotides are marked with asterisks; The open triangles indicate increasing levels of dNTPs.

Silencing of snoRNA-2 transcript eliminated the 2'-O-methylation guided by snoRNA-2—SnoRNA-2 was found to guide the methylation on the guanine nucleotide at position 75 (G75) of the 5.8S rRNA (Levitan, A., et al., 1998. Nucleic Acids Res. 26: 1775-1783). To determine the status of snoRNA-2-guided 2'-O-methylation in the silenced cells, a reverse transcriptase primer extension assay was employed. As is shown in FIG. 7, in the presence of low dNTPs, the reverse transcriptase reaction was stopped at one nucleotide before the methylation site. In addition, the level of methylation at position G75 was reduced by 87% in the silenced cells as compared with wild-type cells (FIG. 7, compare lane 1 to lane 4). On the other hand, the level of methylation of the adenosine at position 43 (A43) was the same in both wild-type and silenced cells, suggesting a specific undermethylation at position G75 of the 5.8S rRNA.

Altogether, these results demonstrate that snoRNA-2 silencing occurs at the mature RNA transcript and not the precursor RNA transcript, and that snoRNA-2 silencing results in decreased snoRNA-2-guided methylation on the 5.8rRNA.

Example 5

Silencing of snoRNA in L. Major and T. Brucei

To find out if the siRNA-mediated snoRNA-2 silencing is unique to the snoRNA-2 cluster or reflects a broader phenomenon, other snoRNA clusters have been targeted, as follows.

Experimental Results

Silencing of snoRNA 270 using antisense RNA—To examine whether snoRNAs can be silenced also in other trypanosomatid species, the SLA1 cluster of L. major was cloned into the pX-neo vector in the opposite direction with respect to the neo gene (i.e., an antisense construct). As described under Materials and Experimental Methods hereinabove, the antisense construct can potentially downregulate both the SLA1 and the 270-nucleotide C/D snoRNA (snoRNA 270) transcripts. Parasites expressing the antisense transcript were selected at high concentrations of G418 (1-1.2 mg/ml) and RNA from wild-type or transfected cells was subjected to primer extension analysis using oligonucleotides complementary to the snoRNA 270, SLA1 or SL RNA transcripts. As is shown in FIG. 8b, while the expression level of sno270 was significantly decreased in the silenced cells, the expression levels of SLA1 or SL RNA remained unchanged. These results demonstrate that silencing of snoRNA 270 can be achieved also in L. major. However, silencing was not observed for SLA1 and the level of snoRNA 92 was only partially reduced (data not shown). These results are in line with the results presented in FIG. 6c, demonstrating a complete silencing for snoRNA-2, yet with a partial silencing for h2 RNA. Altogether, these results suggest that silencing of the C/D snoRNA is more efficient than of the H/ACA RNA.

Figure 9A:
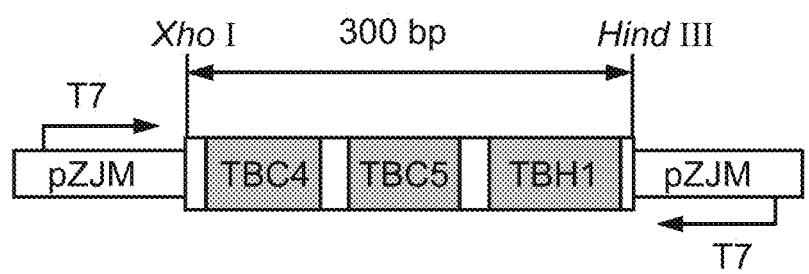
FIGS. 9a-c illustrate silencing of snoRNA in T. brucei by dsRNA.
Figure 9B:
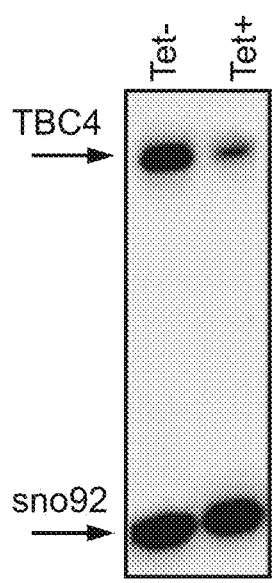
Figure 9C:
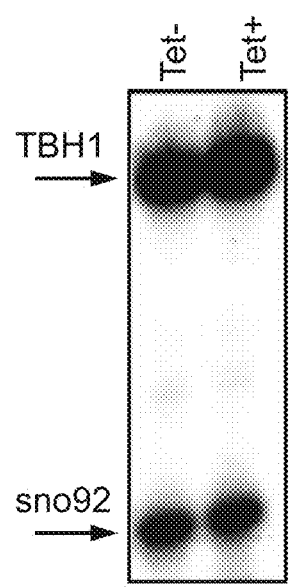

SnoRNA can be silenced in T. brucei by dsRNA—Since siRNAs were detected in snoRNA-2-silenced cells (FIG. 3b) it was suggested that siRNA can be used to silence snoRNAs. Thus, dsRNA targeted against the snoRNA cluster (two C/D RNAs, TBC4 and TBC5; and an H/ACA RNA, TBH1) was prepared by transfection of T. brucei cells with the pZJM expression vector containing the snoRNA cluster between two opposing T7 promoters. In this construct the expression of dsRNA is under the control of the tetracycline repressor. Following two days of tetracycline induction, RNA was prepared and the expression level of TBC4, TBH1 and TBC5 was detected using primer extension analysis. As is shown in FIGS. 9b-c, while the level of TBC4 was significantly decreased in tetracycline induced cells (FIG. 9b), the level of TBH1 (FIG. 9c) and of TBC5 (not shown) remained unchanged. These results demonstrate that dsRNAs produced by the two T7 opposing system are amenable to induce the degradation of C/D snoRNA in T. brucei although at different levels.

Altogether, these results demonstrate that the C/D snoRNA in trypanosomatid species can be efficiently silenced using antisense or dsRNA inhibition.

Example 6

Silencing of snoRNAs in Mammalian Cells

To find out if snoRNAs can be silenced in mammalian cells, the human E14 cells expressing the murine ecotrophic receptor for retroviruses were transfected with an antisense construct targeted against the human U14 snoRNA gene, as follows.

Experimental Results

Silencing of C/D snoRNA in mammalian cells—To find out whether silencing of the C/D snoRNA can operate in mammalian cells, the PRETRO-SUPER expression vector (Brummelkamp T R, Bernards R, Agami R. 2002. A system for stable expression of short interfering RNAs in mammalian cells. Science. 296: 550-3) was used to prepare a U14 snoRNA antisense construct. The silencing construct included the following sequence: 5'-CCAGACATTCG-CAGTTTCCACCAG-3' (SEQ ID NO:43) which is complementary to positions 19-43 of human U14 snoRNA (GenBank Accession No. NR_000022, SEQ ID NO:42, FIG. 10a). The human E14 cells were transfected with the antisense construct and RNA from parental cells or cells carrying the construct was subjected to primer extension analysis. As is shown in FIG. 10b, a 50% reduction in the level of U14 snoRNA was observed in antisense U14 transfected cells as compared with parental cells (FIG. 10b). This reduction was accompanied with a 25% reduction in the level of the methylation guided by this RNA on the cytosine at position 462 (C462) of the 18S rRNA (not shown).

Altogether, these results demonstrate that RNAi silencing can degrade snoRNAs in mammalian cells similar to the silencing observed in trypanosomes.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of downregulating a level of a trypanosoma small nucleolar RNA (snoRNA) in a *T. brucei* trypanosomatid, the method comprising providing an siRNA polynucleotide having a nucleic acid sequence selected suitable for inducing RNAi-mediated degradation of the trypanosoma box C/D domain-containing small nucleolar RNA thereby downregulating the level of the small nucleolar RNA in the *T. brucei* trypanosomatid.

2. The method of claim 1, wherein said snoRNA is selected from the group consisting of *T. brucei* TBC4 snoRNA (SEQ ID NO:35), *T. brucei* snoRNA 92 (SEQ ID NO:37), and *T. brucei* snoRNA 270 (SEQ ID NO:14).

3. The method of claim 1, wherein said trypanosoma snoRNA is involved in ribosomal RNA (rRNA) processing.

4. The method of claim 3, wherein said trypanosoma snoRNA involved in rRNA processing is U3 snoRNA.

5. The method of claim 1, for inhibiting trypanosoma infection in a subject.

6. The method of claim 1, wherein said snoRNA is selected from the group consisting of U3 snoRNA, snoRNA-2, h1 snoRNA, H2 snoRNA, B5 C/D snoRNA, h3 snoRNA, B2 snoRNA, SLA1 RNA, TBC4 snoRNA, TBH1 snoRNA, snoRNA 92, G2 snoRNA, HBII-52 snoRNA, and HBII-85 snoRNA.

7. The method of claim 1, wherein said siRNA polynucleotide is comprised in a nucleic acid construct capable of expressing said siRNA polynucleotide in a cell.

8. The method of claim 7, wherein said nucleic acid construct further comprising a selection marker gene.

9. The method of claim 8, wherein said siRNA polynucleotide is expressed in a reverse orientation to said selection marker gene.

10. The method of claim 7, wherein the nucleic acid construct includes two promoters flanking the isolated polynucleotide, whereas each promoter is capable of directing transcription of a specific strand of the isolated polynucleotide in said trypanosoma.

11. The method of claim 10, wherein each promoter is independently selected from the group consisting of T7 promoter, SP6 promoter, and T3 promoter.

12. The method of claim 10, wherein said two promoters are T7 opposing promoters.

13. The method of claim 1, wherein said siRNA polynucleotide is comprised in a pharmaceutical composition which further comprises a pharmaceutically acceptable carrier.

14. The method of claim 1, wherein said providing is effected by administering to a cell said siRNA polynucleotide.

15. A method of treating trypanosoma infection in a subject, comprising downregulating a level of a trypanosoma small nucleolar RNA (snoRNA) in the infected subject according to the method of claim 1, thereby treating the trypanosoma infection in the subject.

16. A method of downregulating a level of a trypanosoma small nucleolar RNA (snoRNA) in a *T brucei* trypanosomatid, the method comprising providing an siRNA polynucleotide having a nucleic acid sequence selected suitable for inducing RNAi-mediated degradation of the trypanosoma box C/D domain-containing snoRNA 92 (SEQ ID NO:37), thereby downregulating the level of the small nucleolar RNA in the *T. brucei* trypanosomatid.

* * * * *